United States Patent
Wong et al.

(10) Patent No.: US 10,322,180 B2
(45) Date of Patent: Jun. 18, 2019

(54) PHARMACEUTICAL COMPOSITION COMPRISING MODIFIED HEMOGLOBIN-BASED THERAPEUTIC AGENT FOR CANCER TARGETING TREATMENT AND DIAGNOSTIC IMAGING

(71) Applicant: Vision Global Holdings Ltd., Hong Kong (HK)

(72) Inventors: Bing Lou Wong, Irvine, CA (US); Norman Fung Man Wai, Vancouver (CA); Sui Yi Kwok, Hong Kong (HK); Man Kin Wong, Hong Kong (HK); Cornelia Wing Yin Man, Hong Kong (HK)

(73) Assignee: Vision Global Holdings Ltd., Hong Kong (HK)

( * ) Notice: Subject to any disclaimer, the term of this patent is extended or adjusted under 35 U.S.C. 154(b) by 0 days.

(21) Appl. No.: 15/469,978

(22) Filed: Mar. 27, 2017

(65) Prior Publication Data
US 2017/0266285 A1    Sep. 21, 2017

Related U.S. Application Data

(62) Division of application No. 14/275,885, filed on May 13, 2014, now Pat. No. 9,636,404.

(60) Provisional application No. 61/822,463, filed on May 13, 2013.

(51) Int. Cl.
| | |
|---|---|
| *A61K 51/00* | (2006.01) |
| *A61M 36/14* | (2006.01) |
| *A61K 45/06* | (2006.01) |
| *A61K 38/42* | (2006.01) |
| *A61K 49/00* | (2006.01) |
| *A61K 51/08* | (2006.01) |
| *A61K 47/64* | (2017.01) |

(52) U.S. Cl.
CPC ............. *A61K 45/06* (2013.01); *A61K 38/42* (2013.01); *A61K 47/6445* (2017.08); *A61K 49/0043* (2013.01); *A61K 49/0056* (2013.01); *A61K 51/088* (2013.01)

(58) Field of Classification Search
CPC ........ A61K 45/00; A61K 45/06; A61K 31/00; A61K 47/00; A61K 47/48307; A61K 47/6445; A61K 51/00; A61K 51/08; A61K 51/088; A61K 49/00; A61K 49/0043; A61K 49/0056; A61K 38/00; A61K 38/42

USPC ........... 424/1.11, 1.65, 1.73, 9.1, 1.69, 1.81, 424/1.85, 1.89

See application file for complete search history.

(56) References Cited

U.S. PATENT DOCUMENTS 9,636,404 B2 * 5/2017 Wong ..................... A61K 45/06
2005/0059576 A1    3/2005 Adamson et al.

FOREIGN PATENT DOCUMENTS

| EP | 1469011 A1 | 10/2004 |
| JP | H04-230224 A | 8/1992 |
| JP | H09-512796 A | 12/1997 |

OTHER PUBLICATIONS

Adamson et al; BIOT 355-Hemoglobin-drug conjugates for targeted delivery of nucleoside drugs. Abstract of Papers, 234th National Meeting of the American-Chemical-Society. vol. 234; (Aug. 19-23, 2007).
Office Action of CN 201480040021.4 issued from the State Intellectual Property Office of the People's Republic of China dated Jun. 8, 2017.
Office Action from the Japan Patent Office (JPO) dated Jan. 11, 2018.

* cited by examiner

*Primary Examiner* — D. L. Jones
(74) *Attorney, Agent, or Firm* — Spruson & Ferguson (Hong Kong) Limited

(57) ABSTRACT

The present invention provides a pharmaceutical composition containing hemoglobin-based therapeutic agent for treating cancer. The hemoglobin moiety can target cancer cells and the therapeutic moiety (i.e. active agent/therapeutic drug) can kill the cancer cells efficiently. The hemoglobin-based therapeutic agent used in the present invention can be used in the treatment of various cancers such as pancreatic cancer, leukemia, head and neck cancer, colorectal cancer, lung cancer, breast cancer, liver cancer, nasopharyngeal cancer, esophageal cancer, prostate cancer, stomach cancer and brain cancer. The composition can be used alone or in combination with other therapeutic agent(s) such as chemotherapeutic agent to give a synergistic effect on cancer treatment, inhibiting metastasis and/or reducing recurrence. The presently claimed hemoglobin-based 5FU-two-dye conjugate and/or hemoglobin-based 5FU-one-dye conjugate can also be used in live-cell imaging and diagnostic imaging.

4 Claims, 39 Drawing Sheets
Specification includes a Sequence Listing.

Alpha Hemoglobin Chain

```
B   1  MVLSAADKGNVKAAWGKVGGHAAEYGAEALERMFLSFPTTKTYFPHFDLSHGSAQVKGHG   60
H   1  MVLSPADKTNVKAAWGKVGAHAGEYGAEALERMFLSFPTTKTYFPHFDLSHGSAQVKGHG   60
C   1  -VLSPADKTNIKSTWDKIGGHAGDYGGEALDRTFQSFPTTKTYFPHFDLSPGSAQVKAHG   59
P   1  -VLSAADKADVKAAYGEVGAHAGEAGAEALERMFLGFTTTKTYFPHFDLSHGSDEVKAHG   59
E   1  MVLSAADKTNVKAAWSKVGGHAGEFGAEALERMFLGFPTTKTYFPHFDLSHGSAQVKAHG   60
          **. *** *  *.*,**.;  *.;*;.  * .* **********  ** ;**.**

B  61  AKVAAALTKAVEHLDDLPGALSELSDLHAHKLRVDPVNFKLLSHSLLVTLASHLPSDFTP  120
H  61  KKVADALTNAVAHVDDMPNALSALSDLHAHKLRVDPVNFKLLSHCLLVTLAAHLPAEFTP  120
C  60  KKVADALTTAVAHLDDLPGALSALSDLHAYKLRVDPVNFKLLSHCLLVTLACHHPTEFTP  119
P  60  KKVADALTKAVGHLDDMPGALSALSDLHAHKLRVDPVDFKLLSHCLLSTLAVHLPDDFTP  119
E  61  KKVGDALTLAVGHLDDLPGALSNLSDLHAHKLRVDPVNFKLLSHCLLSTLAVHLPNDFTP  120
          **. *** **  *;*.;* ***  ******.******.**  *** *  * ;;***

B 121  AVHASLDKFLANVSTVLTSKYR  142
H 121  AVHASLDKFLASVSTVLTSKYR  142
C 120  AVHASLDKFFAAVSTVLTSKYR  141
P 120  AVHADLDKFLADVSTVLDSKYR  141
E 121  AVHASLDKFLSSVSTVLTSKYR  142
          ****.****;;. ***** ****
```

Beta Hemoglobin Chain

```
B   1  --MLTAEEKAAVTAFWGKVK--VDEVGGEALGRLLVVYPWTQRFFESFGDLSTADAVMKN   56
H   1  MVHLTPEEKSAVTALWGKVN--VDEVGGEALGRLLVVYPWTQRFFESFGDLSTPDAVMGN   58
C   1  --VLSPADKTNIKSTWDKIGGHAGDYGGEALDRTFQSFPTTKTYFPHFDL------SPGS   52
P   1  MVHLSAEEKEAVLGLWGKVN--VDEVGGEALGRLLVVYPWTQRFFESFGDLSNADAVMGN   58
E   1  MVQLSGEEKAAVLALWDKVN--EEEVGGEALGRLLVVYPWTQRFFDSFGDLSNPGAVMGN   58
          *; ;* ; ,* *;  ; ***** *  ;* *; ;* *

B  57  PKVKAHGKKVLDSFSNGMKHLDDLKGTFAALSELHCDKLHVDPENFKLLGNVLVVVLARN  116
H  59  PKVKAHGKKVLGAFSDGLAHLDNLKGTFATLSELHCDKLHVDPENFRLLGNVLVCVLAHH  118
C  53  AQVKAHGKKVADALTTAVAHLDDLPGALSALSDLHAYKLRVDPVNFKLLSHCLLVTLACH  112
P  59  PKVKAHGKKVLQSFSDGLKHLDNLKGTFAKLSELHCDQLHVDPENFRLLGNVIVVVLARR  118
E  59  PKVKAHGKKVLHSFGEGVHHLDNLKGTFAALSELHCDKLHVDPENFRLLGNVLVVVLAPH  118
         ;******** ;;   ;; ;* ***;* *;;; **;**, ;*;*** **;**.. ;; .**

B 117  FGKEFTPVLQADFQKVVAGVANALAHRYH
H 119  FGKEFTPPVQAAYQKVVAGVANALAHKYH
C 113  HPTEFTPAVHASLDKFFAAVSTVLTSKYR
P 119  LGHDFNPNVQAAFQKVVAGVANALAHKYH
E 119  FGKDFTPELQASYQKVVAGVANALAHKYH
         ;*.* ;.* ;*.,*.*.;;*; *;
```

FIG. 2

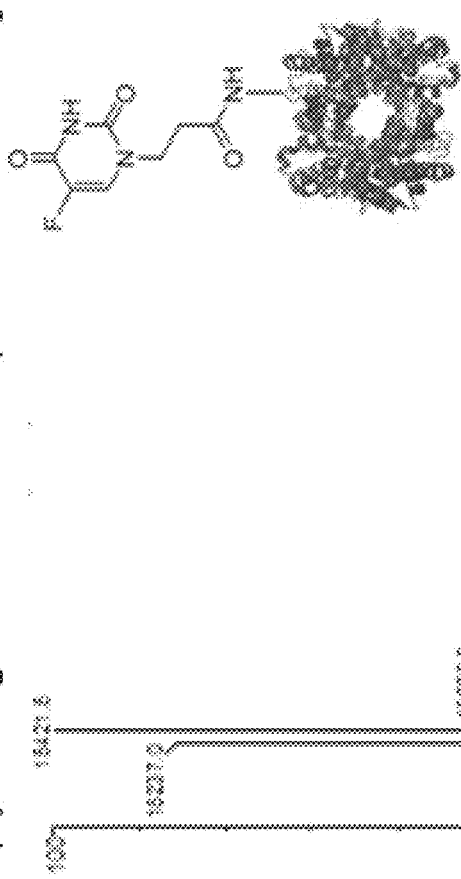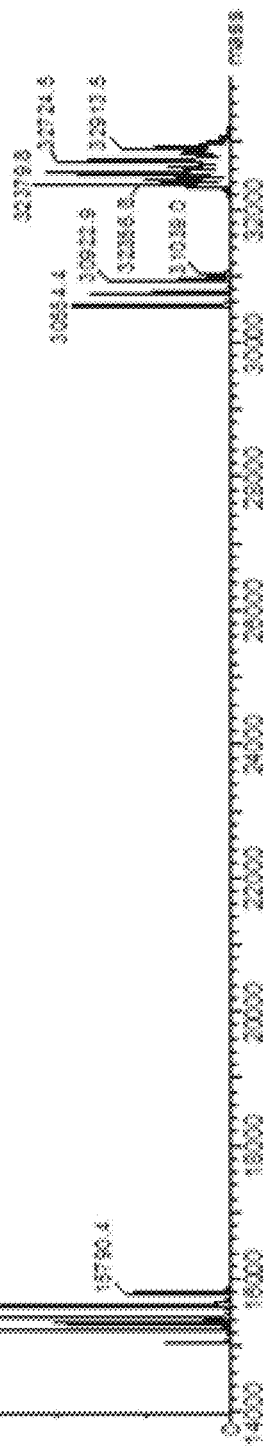
FIG. 5B (B)
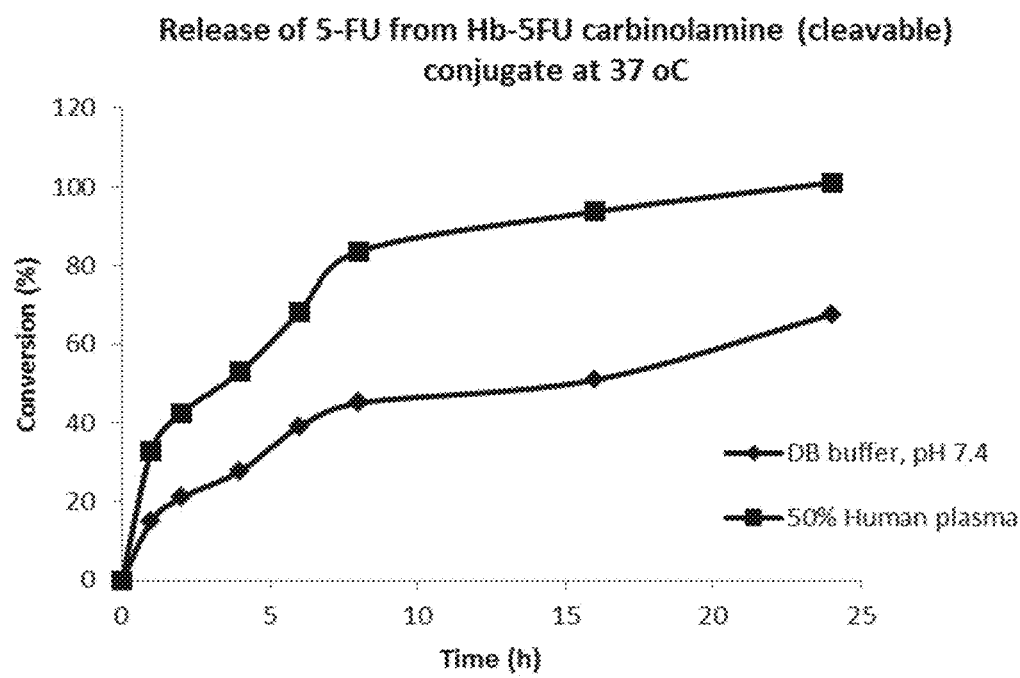
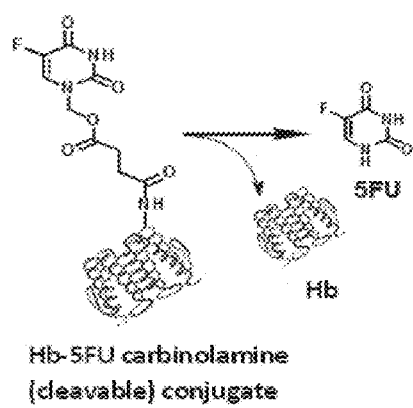
Hb-5FU carbinolamine
(cleavable) conjugate
FIG. 6B Cleavable conjugate: Hb-5FU-carbinolamine (cleavable) conjugate;

Non-cleavable conjugate: Hb-5FU-alkyl (non-cleavable) conjugate.

Cleavable conjugate: Hb-5FU-carbinolamine (cleavable) conjugate;

Non-cleavable conjugate: Hb-5FU-alkyl (non-cleavable) conjugate.

Cleavable conjugate: Hb-5FU-carbinolamine (cleavable) conjugate;

Non-cleavable conjugate: Hb-5FU-alkyl (non-cleavable) conjugate.

Cleavable conjugate: Hb-5FU-carbinolamine (cleavable) conjugate;

Non-cleavable conjugate: Hb-5FU-alkyl (non-cleavable) conjugate.

Cleavable conjugate: Hb-5FU-carbinolamine (cleavable) conjugate;

Non-cleavable conjugate: Hb-5FU-alkyl (non-cleavable) conjugate.

Tumor growth of CD133+ Liver cancer stem cell animal model (HepG2)

Cleavable conjugate: Hb-5FU-carbinolamine (cleavable) conjugate;

Non-cleavable conjugate: Hb-5FU-alkyl (non-cleavable) conjugate.

Tumor growth of CD44+CD24- Breast cancer stem cell animal model (MCF7)

Cleavable conjugate: Hb-5FU-carbinolamine (cleavable) conjugate;

Non-cleavable conjugate: Hb-5FU-alkyl (non-cleavable) conjugate.

*, p < 0.05 compare to control

Cleavable conjugate: Hb-5FU-carbinolamine (cleavable) conjugate;

Non-cleavable conjugate: Hb-5FU-alkyl (non-cleavable) conjugate.

\*\*, p < 0.001 compare to control

Cleavable conjugate: Hb-5FU-carbinolamine (cleavable) conjugate;

Non-cleavable conjugate: Hb-5FU-alkyl (non-cleavable) conjugate.

Cleavable conjugate: Hb-5FU-carbinolamine (cleavable) conjugate;

Non-cleavable conjugate: Hb-5FU-alkyl (non-cleavable) conjugate.

*, p < 0.05 compare to control; **, p < 0.001 compare to control

Cleavable conjugate: Hb-5FU-carbinolamine (cleavable) conjugate;

Non-cleavable conjugate: Hb-5FU-alkyl (non-cleavable) conjugate.

**, p < 0.001 compare to control

Cleavable conjugate: Hb-5FU-carbinolamine (cleavable) conjugate;

Non-cleavable conjugate: Hb-5FU-alkyl (non-cleavable) conjugate.

*, p < 0.05 compare to control

Cleavable conjugate: Hb-5FU-carbinolamine (cleavable) conjugate;

Non-cleavable conjugate: Hb-5FU-alkyl (non-cleavable) conjugate.

(A)

Disulfide
(A)
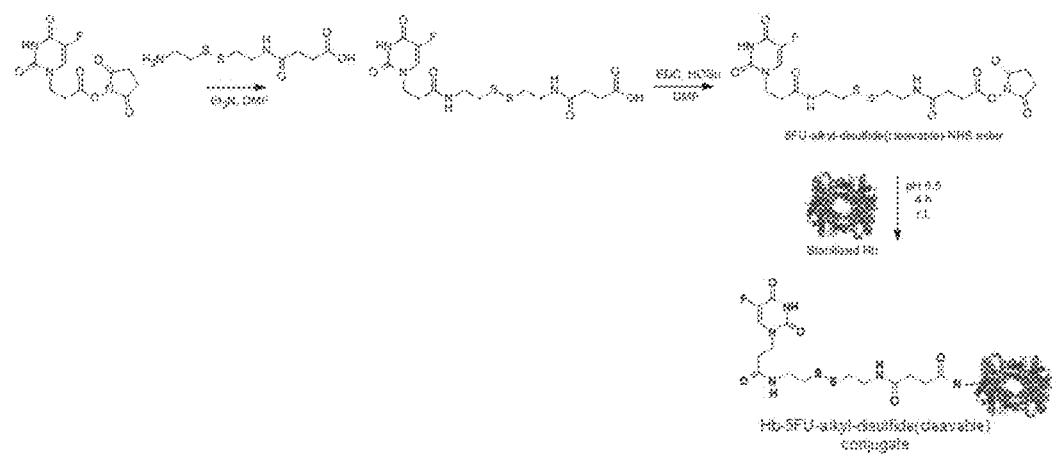
(B)
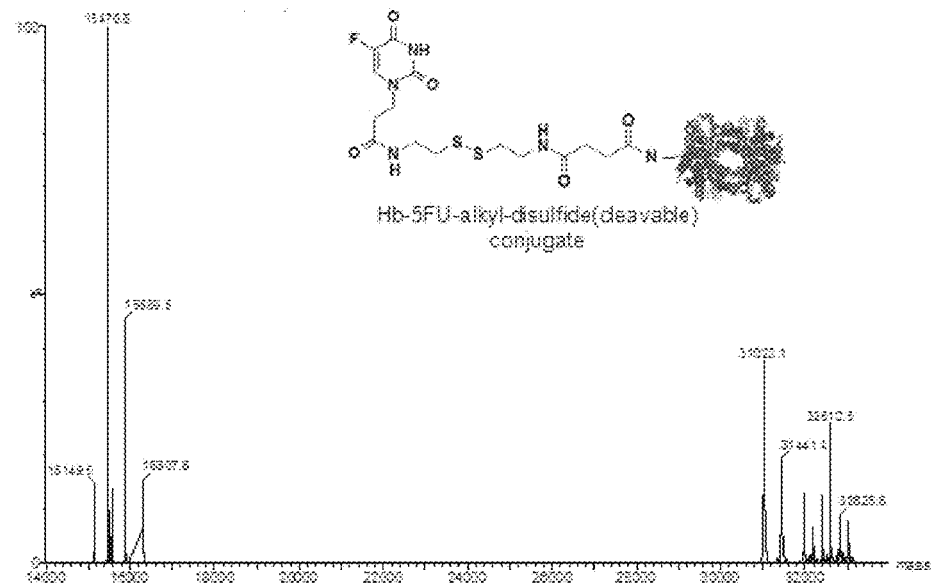
FIG. 29

One-Dye compound – Hemoglobin labeled with 5FU (non-cleavable) and Fluorescein
Name = Hb-5FU-alkyl (non-cleavable)-FL conjugate
Modification:
(A)
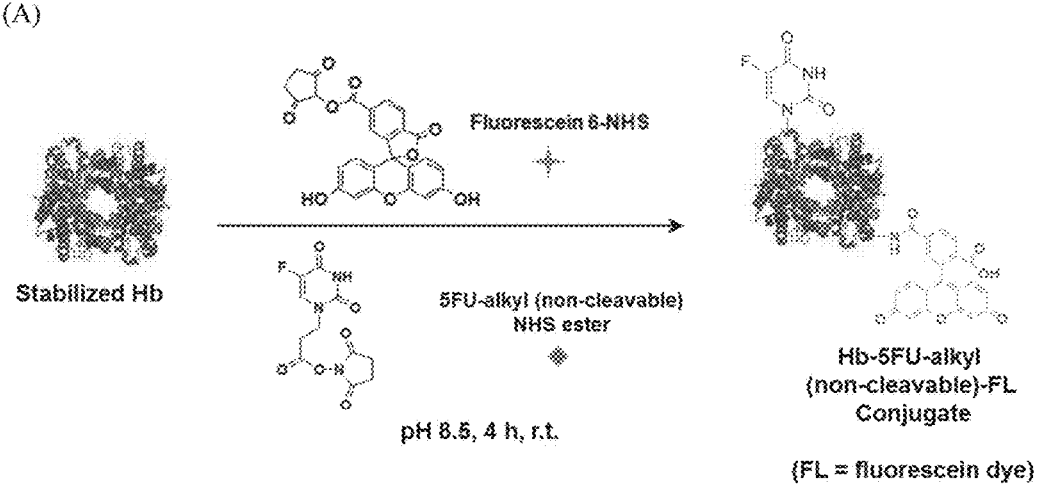
(B)
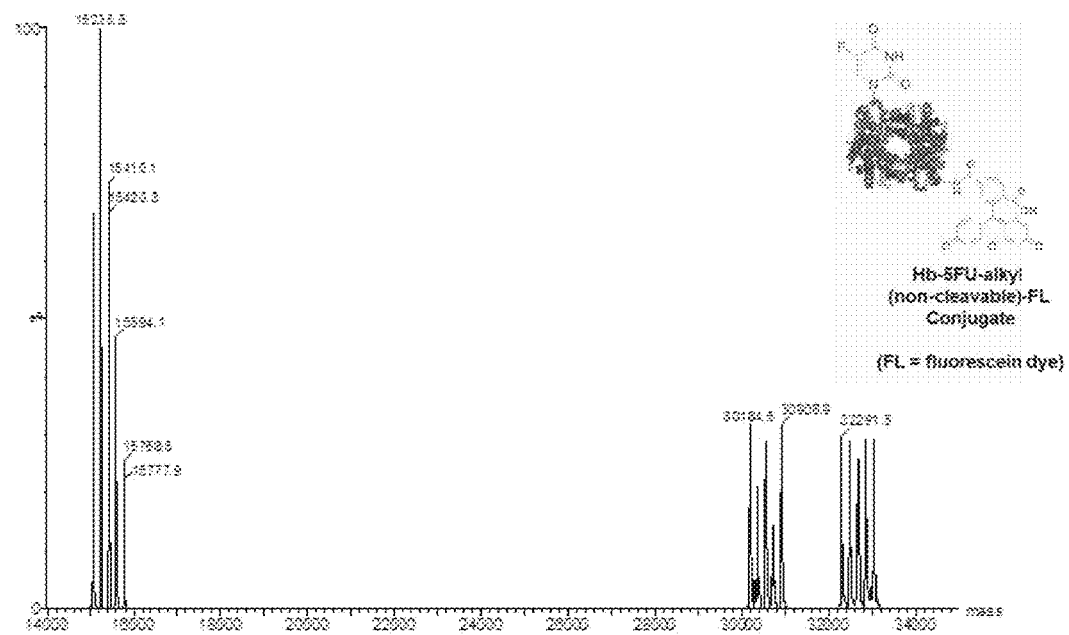
FIG. 30

One-Dye conjugate for imaging – Hemoglobin labeled with 5FU (cleavable) and Fluorescein
Name = Hb-5FU-carbinolamine (cleavable)-FL conjugate
Modification:
(A)
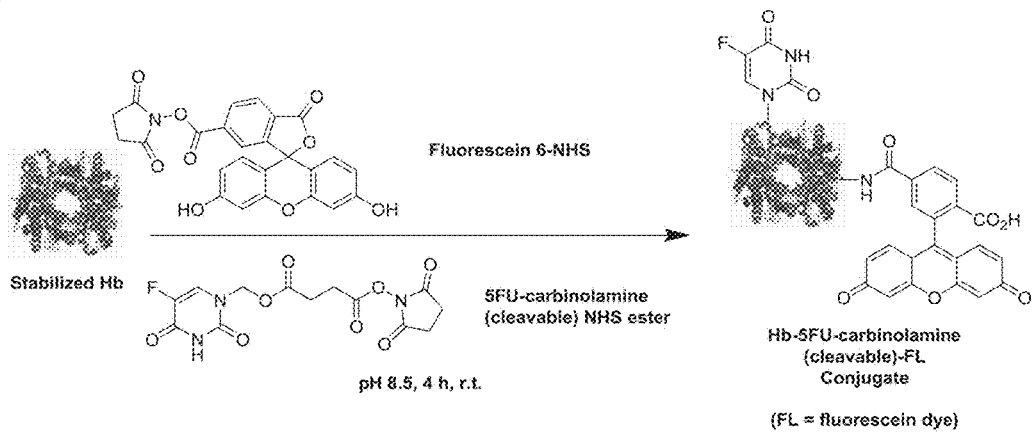
(B)
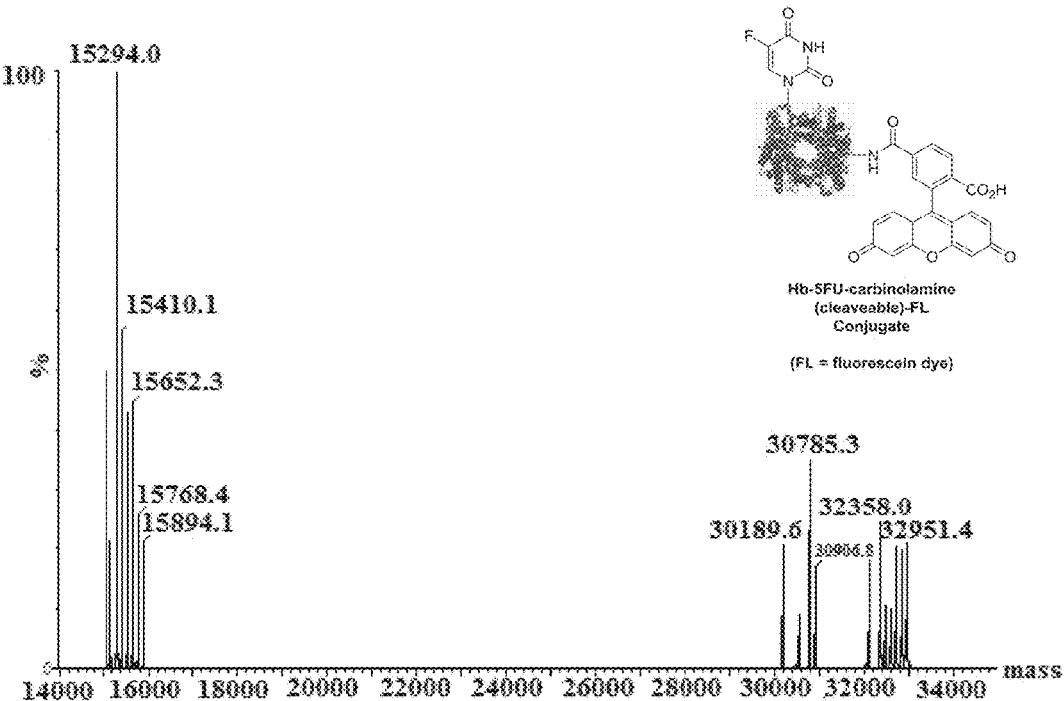
FIG. 31

Two-dyes conjugate for imaging
Name: Hb-5FU-Dan-TAM conjugate
(A)
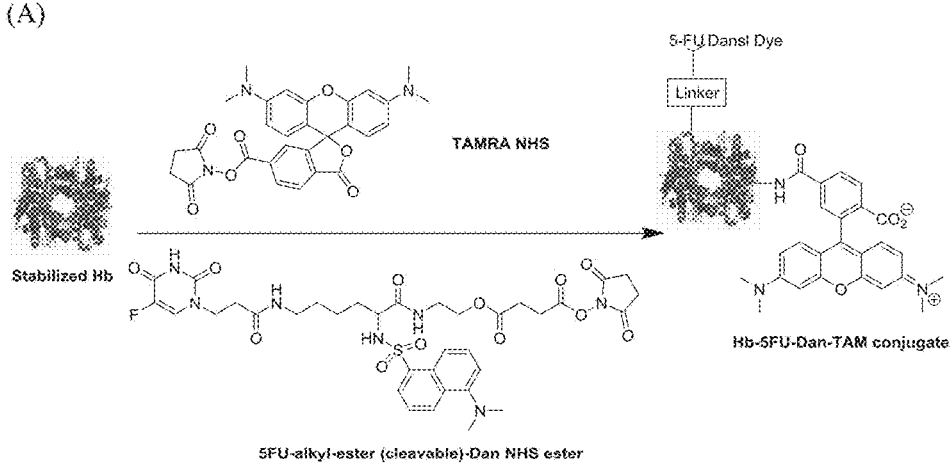
(B)
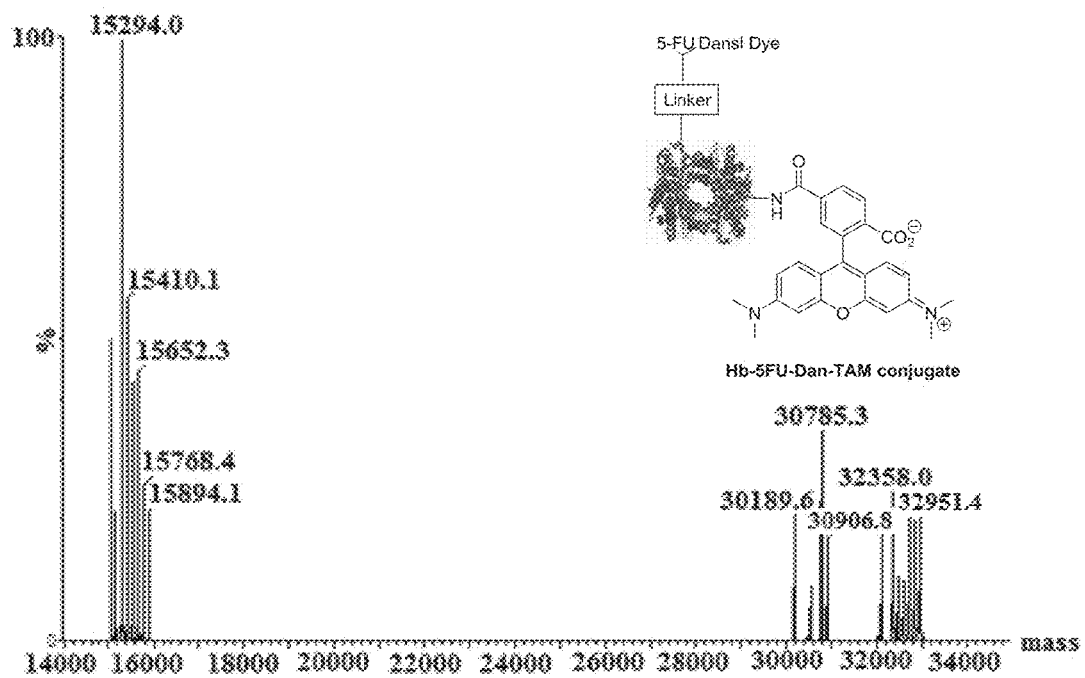
FIG. 32

PHARMACEUTICAL COMPOSITION COMPRISING MODIFIED HEMOGLOBIN-BASED THERAPEUTIC AGENT FOR CANCER TARGETING TREATMENT AND DIAGNOSTIC IMAGING

CROSS-REFERENCE TO RELATED APPLICATION

The present application is a divisional application of U.S. non-provisional application Ser. No. 14/275,885 filed on May 13, 2014 which claims priority from a US provisional patent application under the Ser. No. 61/822,463 filed May 13, 2013, and the disclosure of which is incorporated herein by reference in its entirety.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2014, Vision Global Holdings Limited, All Rights Reserved.

TECHNICAL FIELD

The present invention describes hemoglobin-based therapeutic agent that has been chemically modified to create a material having the ability of targeting the cancer cells. The present invention further describes a design for chemical engineering for creating a hemoglobin-based therapeutic agent. The present invention further relates to hemoglobin-based therapeutic agent containing pharmaceutical compositions for cancer targeting treatment in humans and other animals, in particular, for liver cancer, breast cancer, pancreatic cancer, and tumor induced or associated with respective progenitor cells. Also, the present invention provides a fluorescent labeled modified hemoglobin used in live-cell imaging and diagnostic imaging.

BACKGROUND OF INVENTION

Chemotherapy is the use of anticancer drugs to treat cancerous cells. Chemotherapy has been used for many years and is one of the most common treatments for cancer. In most cases, chemotherapy works by interfering with the cancer cell's ability to grow or reproduce. Different groups of drugs work in different ways to fight cancer cells. Chemotherapy may be used alone for some types of cancer or in combination with other treatments such as radiation (or radiotherapy) or surgery. Often, a combination of chemotherapy drugs is used to fight a specific cancer. There are over 50 chemotherapy drugs that are commonly used.

While chemotherapy can be quite effective in treating certain cancers, chemotherapy drugs reach all parts of the body, not just the cancer cells. Because of this, there may be many side effects during treatment. Therefore, there is a need having a method for lowering the dosage of chemotherapy drugs to alleviate the side effects and maintain its efficacy during cancer treatment. For lowering the dosage, it can benefit both patient (lesser side effects) and manufacturer for chemotherapeutic drug (lower production cost).

Common radiotherapeutic agents include Rhodium-105 complex, Samarium-153 complex and other related complex; these agents also have a lot of side effects for cancer patients.

Hypoxia is common in cancers. Hypoxia and anemia (which contributes to tumor hypoxia) can lead to ionizing radiation and chemotherapy resistance by depriving tumor cells of the oxygen essential for the cytotoxic activities of these agents. Hypoxia may also reduce tumor sensitivity to radiation therapy and chemotherapy through one or more indirect mechanisms that include proteomic and genomic changes.

Thus, there is a need in the art for improved cancer treatments that target cancerous cells and tissues while reducing the effects of cancer treatments on non-cancerous cells and tissues.

SUMMARY OF INVENTION

In the present invention, a hemoglobin-based therapeutic agent targeting cancer cells in order to efficiently kill cancer cells by a therapeutic drug (e.g. chemotherapeutic agent, radiotherapeutic agent) is provided. Common chemotherapeutic and radiotherapeutic agents are widely used in different patients, however many side-effects are found. These problems may be overcome by chemically modifying hemoglobin and linking it to one or more therapeutic drugs. When compared to well known therapeutic drugs for cancer (e.g. chemotherapeutic drug including 5-Fluorouracil, Temozolomide, Cisplatin), the hemoglobin-based therapeutic agents of the present invention not only can target cancer cells, but are much more efficacious in the treatment of tumors. Further, since the cancer-targeting hemoglobin-based therapeutic agents can be used in low doses, the adverse side effect from the therapeutic drug is greatly decreased.

Most therapeutic drugs are very expensive. The treatment cost can be cut down significantly for each patient if the therapeutic dose is lowered. Hemoglobin-based therapeutic agent is a good approach for lowering the therapeutic dose as the modified hemoglobin can be targeted to cancer cells.

The presently claimed hemoglobin-based therapeutic agent can also be linked to fluorescent probe(s) to facilitate the live-cell imaging and diagnostic imaging. Namely, the hemoglobin-based therapeutic agent conjugated with fluorescein can be uptaken into liver cancer cells and breast cancer cells. The uptake of freshly fluorescein conjugated hemoglobin-based therapeutic agents by cells is verified by immediately employing the same to the cells in a series of live cell uptake studies as described hereinafter. The fluorescein conjugated hemoglobin-based therapeutic agent is observed to be uptaken into liver cancer cells (e.g. HepG2 cell line) and breast cancer cells after 15 min of exposure and the signals peak after 1 hour of exposure.

One or more fluorescein molecules (e.g. seven fluorescein molecules) can be linked to one molecule of stabilized hemoglobin in order to enhance the signal for live-cell imaging and diagnostic imaging. The present invention also compares a hemoglobin-based therapeutic agent conjugated with and without fluorescent probe(s) to target the cancer cells for cancer treatment. In a comparative study of the present invention, the dosage of the hemoglobin-based therapeutic agent can be lowered down when compared to therapeutic drug alone. The result supports that the presently claimed hemoglobin-based therapeutic agent can greatly alleviate the side effects derived from the therapeutic drug.

Therefore, the first aspect of the present invention is to construct a chemically modified hemoglobin with one or more functional groups that can be used as a linkage to therapeutic drug for targeting the cancer cells. The second aspect of the present invention is to chemically link the modified hemoglobin or stabilized hemoglobin to therapeutic drug (active agent) via cleavable or non-cleavable linkage or linker in order to kill the cancer cells. The therapeutic drug or active agent which can be linked to the hemoglobin molecule of the present invention includes but not limited to chemotherapeutic drug, e.g., 5-Fluorouracil, Temozolomide, Cisplatin, or radiotherapeutic drug, e.g., Rhodium-105 complex, Samarium-153 complex and other related complex, or any other therapeutic drug or compound which is proved to be effective for treating or alleviating cancer and capable of being readily linked to the hemoglobin molecule of the present invention, through said linker to the stabilized hemoglobin molecule or with the chemically modified hemoglobin molecule. Besides linking to therapeutic drug, the stabilized or modified hemoglobin molecule of the present invention can also be linked to cell or fluorescent labeling agent including but not limited to fluorescent proteins, non-protein organic fluorophores, fluorescent nano-particles and metal-based luminescent dye.

The present invention further relates to hemoglobin-based therapeutic agent containing pharmaceutical compositions for targeted cancer treatment in humans and other animals. The composition includes a therapeutically effective mount of said therapeutic agent and a pharmaceutically acceptable carrier, salt, buffer, water, or a combination thereof, in order for treating cancer. The third aspect of the present invention is to provide a method of using the hemoglobin-based therapeutic agent containing pharmaceutical composition of the present invention for treating cancer by administering said composition to a subject in need thereof suffering from various tumors and cancers. Said composition can be administered to the subject by various routes including but not limited to intravenous injection, intraperitoneal injection, and subcutaneous injections. Both cleavable and non-cleavable forms of the hemoglobin-based therapeutic agent contains an active agent such as chemotherapeutic agent (e.g. 5-Fluorouracil, 5FU), which reveals efficacies when tested in both in vitro and in vivo cancer models, including liver cancer (hepatocellular carcinoma), colorectal cancer, non-small cell lung cancer, leukemia, glioblastoma, and breast cancer (triple negative breast cancer), and pancreatic cancer.

The hemoglobin-based therapeutic agent of the present invention is also chemically modified to facilitate the targeting of the therapeutic agent to cancer cells such that it is more efficient to kill cancer cells. Hemoglobin (Hb) can be chemically modified and linked to different therapeutic agents (e.g. 5FU, Temozolomide, Cisplatin, etc). Hemoglobin from different sources is a protein that targets to cancer cells. This targeting property facilitates killing cancerous cells, cancer stem cells and/or cancer progenitor cells efficiently. As such, dose of the therapeutic agent can be lowered.

The hemoglobin-based therapeutic agent used in the present invention can be used in the treatment of various cancers such as pancreatic cancer, leukemia, head and neck cancer, colorectal cancer, lung cancer, breast cancer, liver cancer, nasopharyngeal cancer, esophageal cancer and brain cancer. The present invention is directed to hemoglobin-based therapeutic agent, to methods of treating cancer, and to methods of treating and/or inhibiting metastasis of cancerous tissue and recurrence of cancerous tissue, including but not limited to liver cancer (which can be exemplified in liver cancer progenitor cells-induced tumor xenograft model), breast cancer, especially triple negative breast cancer (which can be exemplified in triple negative progenitor cells-induced tumor xenograft model). Cells within a tumor are heterogeneous in nature. It is generally thought to be made up of (1) a majority of cancer cells with limited ability to divide, and (2) a rare population of cancer stem-like cells (CSCs), also known as progenitor cells, which can form new tumor cells and are highly metastatic in nature. Due to their inherent properties of being chemoresistant and metastatic, CSCs have been postulated to be responsible for recurrence in cancer patients. The tumor progenitor cells-induced mice models as described in one of the embodiments of the present invention are the best representative model of tumor metastasis and recurrence.

As hemoglobin moiety can bring the oxygen to kill cancer stem cells while therapeutic agent moiety can kill the cancer cells, the hemoglobin-based therapeutic agent of the present invention is to give a synergistic effect in cancer treatment.

BRIEF DESCRIPTION OF THE DRAWINGS

FIG. 2 shows the amino acid sequence of hemoglobin from different species.

FIG. 5B shows the LC-MS results for modified hemoglobin-based 5FU (non-cleavable conjugate).

FIG. 6B shows the release of 5FU from hemoglobin-based 5FU conjugate (Hb-5FU-carbinolamine (cleavable) conjugate) in HPLC studies.

FIG. 29 shows the (A) schematic scheme and (B) characterization of 5FU modified hemoglobin conjugate with cleavable disulfide linker (5FU-alkyl-disulfide (cleavable) NHS ester) by ESI-MS method.

FIG. 30 shows the (A) schematic scheme and (B) characterization of fluorescent-labeled 5FU modified hemoglobin conjugate with alkyl non-cleavable linker (Hb-5FU-alkyl(non-cleavable) FL conjugate) by ESI-MS method.

FIG. 31 shows the (A) schematic scheme and (B) characterization of fluorescent-labeled 5FU modified hemoglobin conjugate with carbinolamine cleavable linker (Hb-5FU-carbinolamine (cleavable) FL conjugate) by ESI-MS method.

FIG. 32 shows the (A) schematic scheme and (B) characterization of 5FU modified hemoglobin conjugate with two fluorescent dyes labeling (Hb-5FU-Dan-TAM).

DEFINITIONS

The term "cancer stem cell" refers to the biologically distinct cell within the neoplastic clone that is capable of initiating and sustaining tumor growth in vivo (i.e. the cancer-initiating cell).

The term "cleavable conjugate" refers to the conjugate with at least one cleavable linker and it can easily release the linked therapeutic drug/active agent by hydrolysis or redox reaction.

The term "non-cleavable conjugate" refers to the conjugate with at least one non-cleavable linker and it cannot easily release the linked therapeutic drug/active agent by hydrolysis or redox reaction.

DETAILED DESCRIPTION OF INVENTION

As discussed in the background, most cancerous tissues, such as cancerous tumors, are hypoxic. Hemoglobin can be used to alleviate the hypoxic condition. Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Naturally-occurring hemoglobin is a tetramer which is generally stable when present within red blood cells. However, when naturally-occurring hemoglobin is removed from red blood cells, it becomes unstable in plasma and splits into two $\alpha$-$\beta$ dimers. Each of these dimers is approximately 32 kDa in molecular weight. These dimers may cause substantial renal injury when filtered through the kidneys and excreted. The breakdown of the tetramer linkage also negatively impacts the sustainability of the functional hemoglobin in circulation.

In one embodiment of the present invention, the hemoglobin is stabilized by a cross-linker to form the stabilized tetramer. The stabilized hemoglobin has the oxygen transport feature and it can target cancerous cells or tissues in a human or animal body. The hemoglobin-based oxygen carrier is chemically modified and linked to the chemotherapeutic agent triggering a receptor-mediated mechanism and leading a combined chemotherapeutic agent to localize together in the cytoplasm of the cancerous cells in order to increase the efficacy of both hemoglobin-based oxygen carrier and the chemotherapeutic agent.

Figure 1:
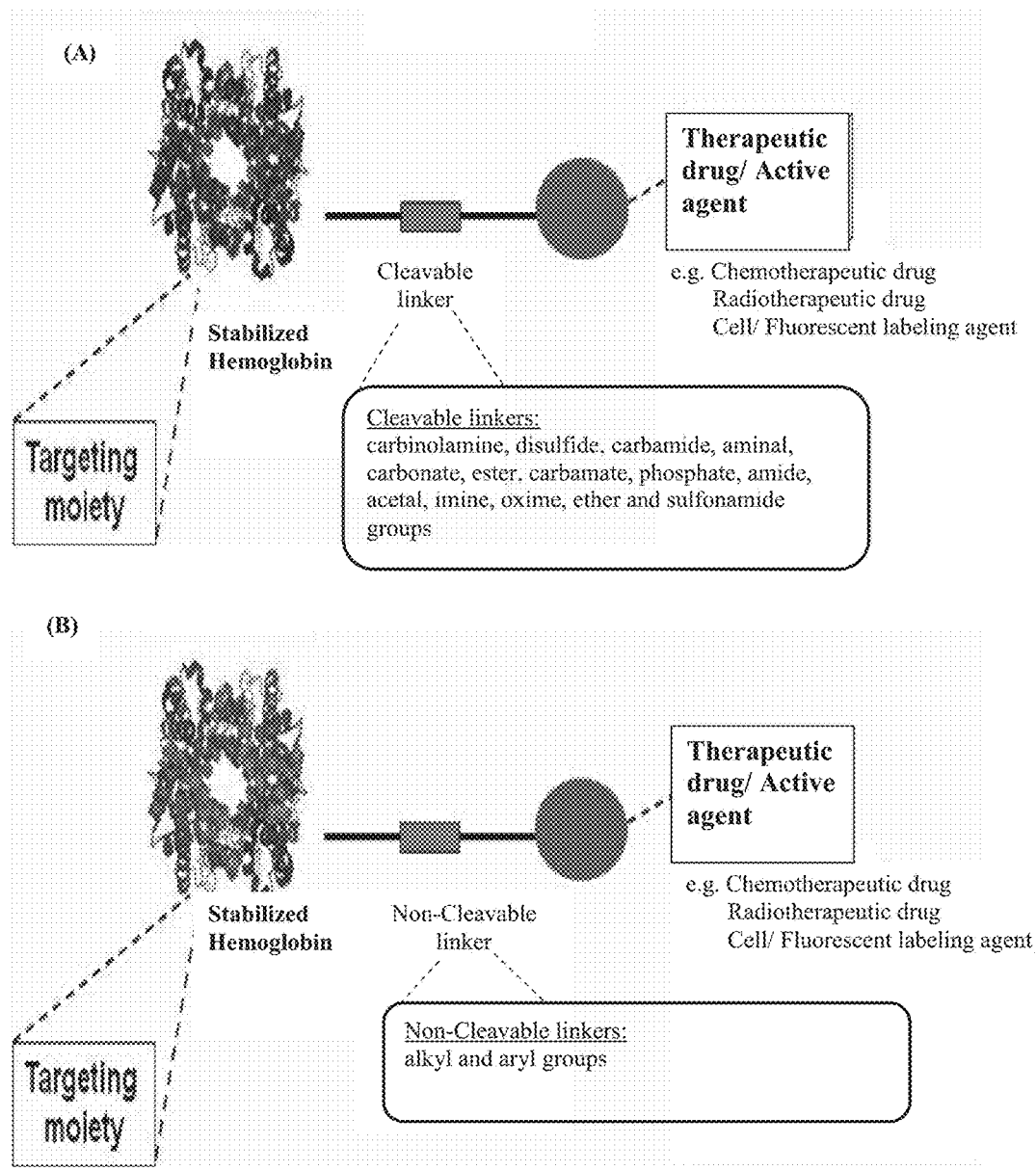
FIG. 1 shows the design approach for construction of hemoglobin-based therapeutic agent. One or more therapeutic drugs can be linked to modified hemoglobin to form the hemoglobin-based therapeutic agent. The modified hemoglobin or stabilized hemoglobin can be chemically linked to therapeutic agent via cleavable (1A) or non-cleavable linkage (1B).

A design for construction of a hemoglobin-based therapeutic drug is shown in FIG. 1A and FIG. 1B. One or more active agents (or "therapeutic drug" used interchangeably herein) are linked to the modified or stabilized hemoglobin to form the presently claimed hemoglobin-based therapeutic agent. The selection of one or more particular active agent(s) can be made depending upon the type of cancer tissue to be targeted and the desired molecular size of the resulting chemically modified product. Further, the selected active agents may be the same or different in the case of more than one active agents. That is, an active agent, etc., as long as the resultant molecule retains the efficacy and is also able to link with stabilized hemoglobin for targeting the cancer cells. The modified hemoglobin or stabilized hemoglobin can be chemically linked to therapeutic drug/active agent via cleavable (FIG. 1A) or non-cleavable linkage (FIG. 1B). Different constructs for chemical modification of hemoglobin can be prepared in the present invention and the stabilized hemoglobin can be linked to the therapeutic drug/active agent.

Some therapeutic drugs (e.g. chemotherapeutic drug, 5FU) cannot be used in high dose because of high toxicity. In the present invention, the chemotherapeutic agent, 5FU, is chemically linked to the stabilized hemoglobin (~65 kDa). The source of hemoglobin can be from, but not limited to, bovine, human, canine, porcine, equine and recombinant hemoglobin and/or subunits. FIG. 2 shows the amino acid sequences alignment of bovine, human, canine, porcine and equine hemoglobin, respectively labeled B, H, C, P, and E (SEQ ID NOS. 1-5 for alpha hemoglobin chain of bovine, human, canine, porcine and equine, respectively; SEQ ID NOS. 6-10 for beta hemoglobin chain of bovine, human, canine, porcine and equine, respectively). The unlike amino acids from various sources are shaded. FIG. 2 indicates that human hemoglobin shares high similarity with bovine, canine, porcine and equine when comparing their amino acid sequences.

Figure 3A:
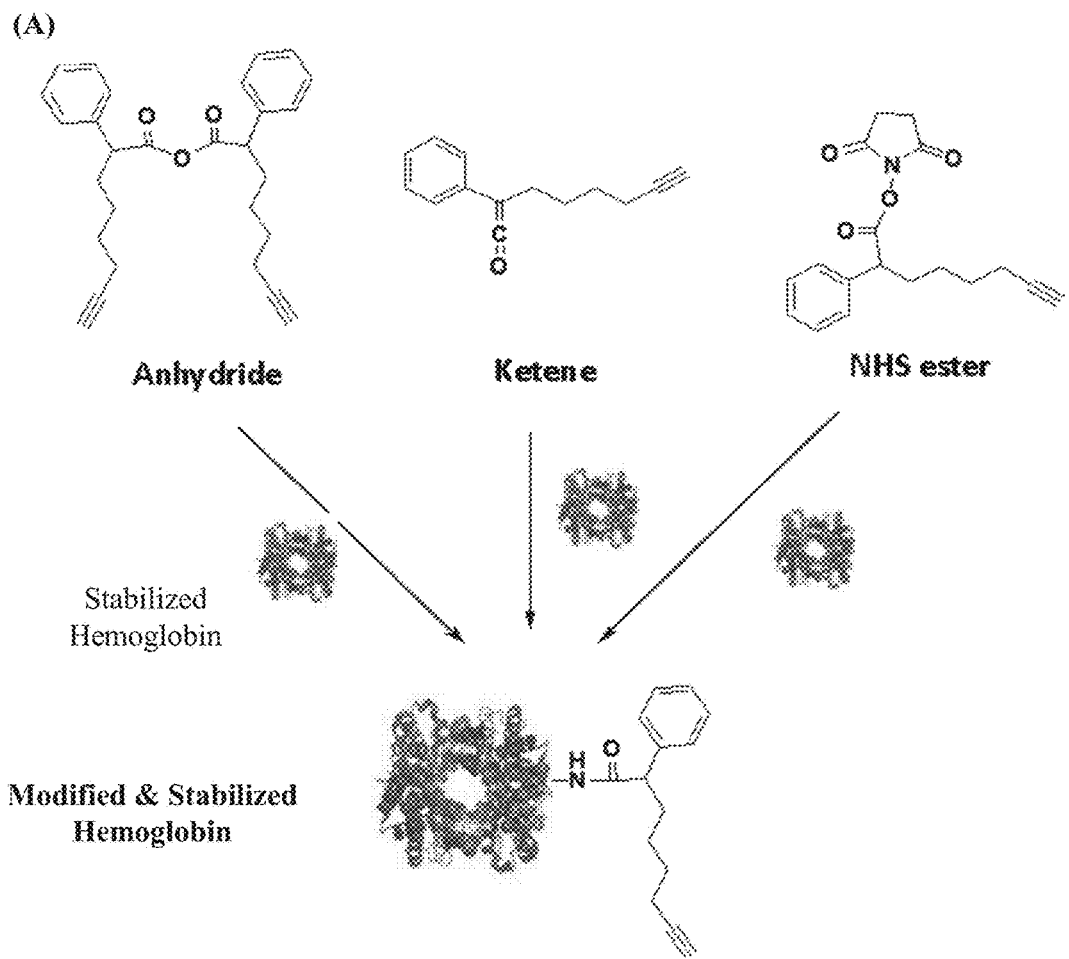
FIG. 3A shows the chemically modified hemoglobin by (1) Anhydride, (2) Ketene and (3) NHS ester.
Figure 3B:
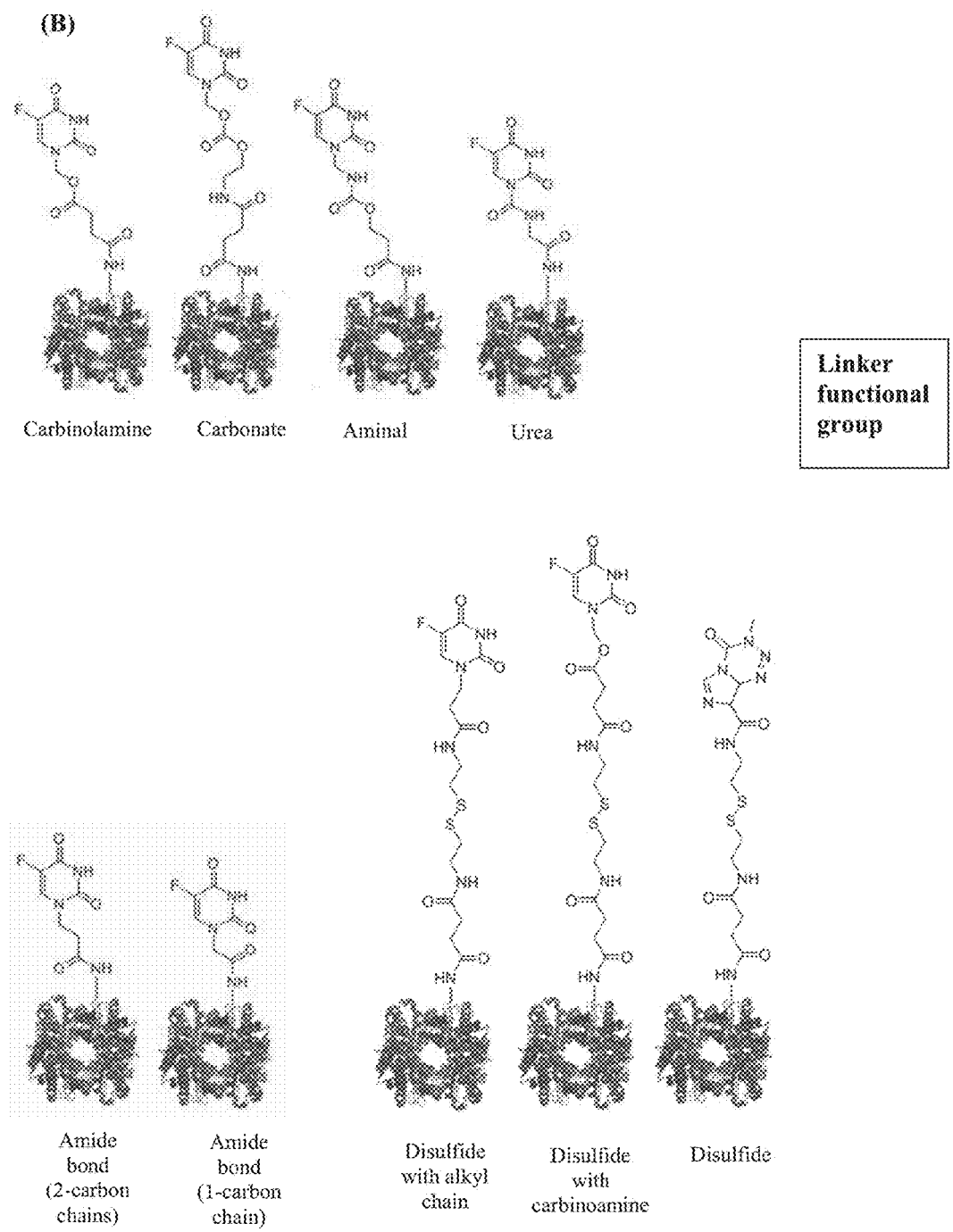
FIG. 3B shows the chemically modified hemoglobin by (1) Carbinolamine, (2) Carbonate, (3) Aminal, (4) Urea, (5) Amide (2-carbon chains), (6) Amide (1-carbon chain), (7) Disulfide with alkyl chain, (8) Disulfide with carbinolamine and (9) Disulfide.

The hemoglobin can be modified chemically by different functional groups before linking to the therapeutic drug. The hemoglobin can be modified by (1) anhydride, (2) ketene, (3) NHS ester, (4) isothiocyanates, (5) isocyanates, (6) activated esters (e.g. fluorophenyl esters, and carbonyl azides), (7) sulfonyl chlorides, (8) carbonyls followed by reductive amination, (9) epoxides, (10) carbonates, (11) fluorobenzenes, (12) imidoesters, (13) hydroxymethyl phosphine derivatives, (14) maleimides, (15) alkyl halides or haloacetamides, (16) disulfides, (17) thiosulfates, (18) aziridine-containing reagents, (19) acryloyl derivatives, (20) arylating agents, (21) vinylsulfone derivatives, (22) native chemical ligation (e.g. thioesters), (23) periodate oxidation of N-terminal serine or threonine to generate aldehydes for coupling with hydroxylamines, hydrazines, or hydrazides, (24) carbodiimides, (25) 4-sulfo-2,3,5,6-tetrafluorophenol, (26) carbonyl diimidazole, (27) sulfo-NHS, (28) diazoalkanes and diazoacetyl compounds, (29) Mannich condensation, (30) diazonium derivatives, (31) diazirine derivatives, (32) benzophenones and anthraquinones, (33) N-terminal modification by pyridoxal-5-phoshpate-based biomimetic transamination, (34) incorporation of bioorthogonal functionalities (e.g. alkynes and azides) with subsequent bioorthogonal conjugation reactions (e.g. dipolar addition Huisgen 1,3-dipolar additions of alkynes and azides, Staudinger ligation of azides and triarylphosphines, Diels-Alder reaction of alkenes and tetrazines, photochemical reaction of alkenes and tetrazoles), (35) metal carbenoids, (36) palladium-activated allyl reagents, (37) photoaffinity labeling agents. FIG. 3A shows the chemically modified hemoglobin by (1) anhydride, (2) ketene and (3) NHS ester. FIG. 3B shows the chemically modified hemoglobin by (1) carbinolamine, (2) carbonate, (3) aminal, (4) urea, (5) amide (2-carbon chains), (6) amide (1-carbon chain), (7) disulfide with alkyl chain, (8) disulfide with carbinolamine and (9) disulfide. On the other hand, the stabilized hemoglobin can be directly linked to therapeutic drug and/or fluorescent agent via cleavable or non-cleavable linkers.

Figure 4A:
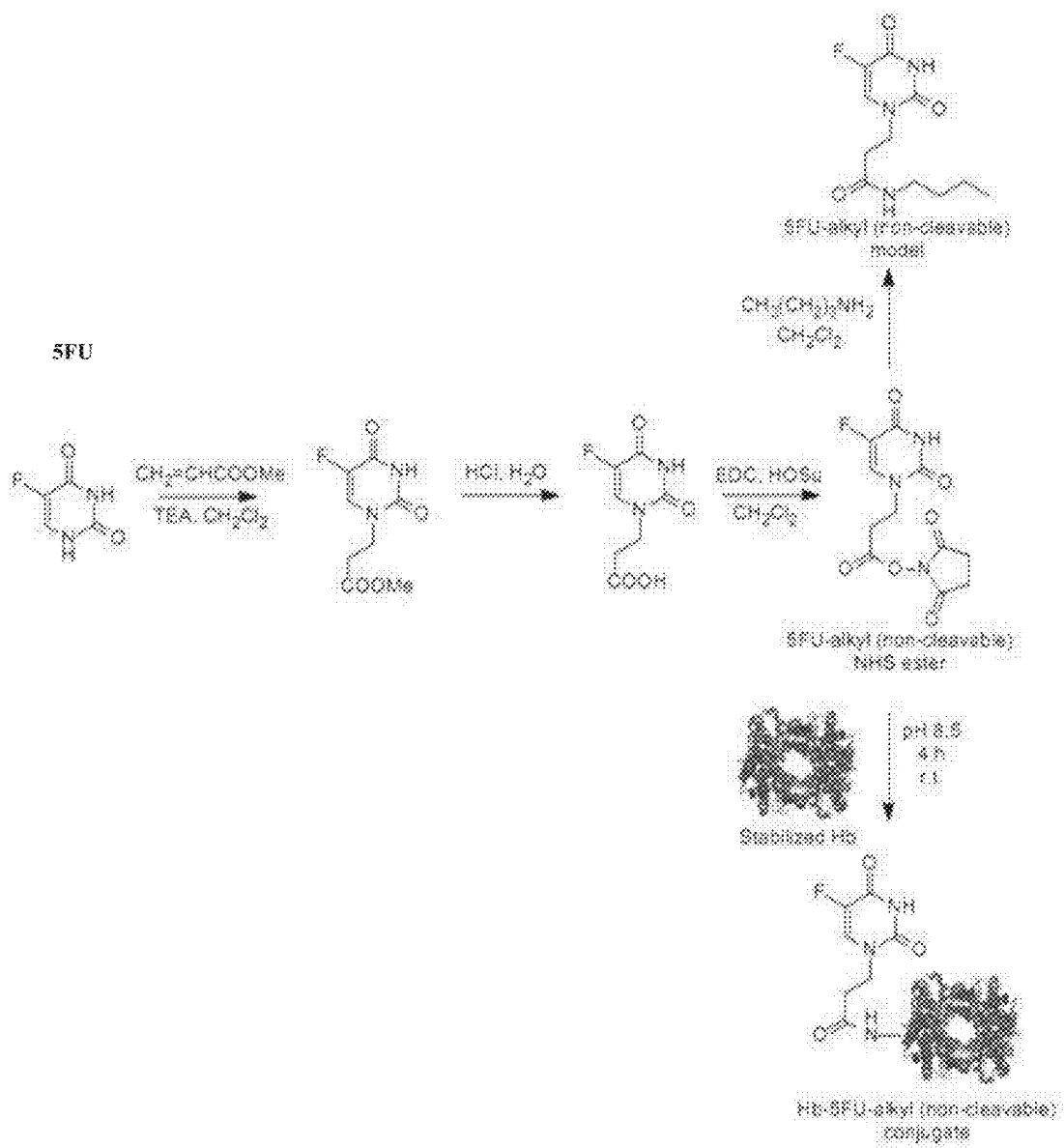
FIG. 4A shows the synthetic scheme for Hb-5FU-alkyl (non-cleavable) conjugate.
Figure 4B:
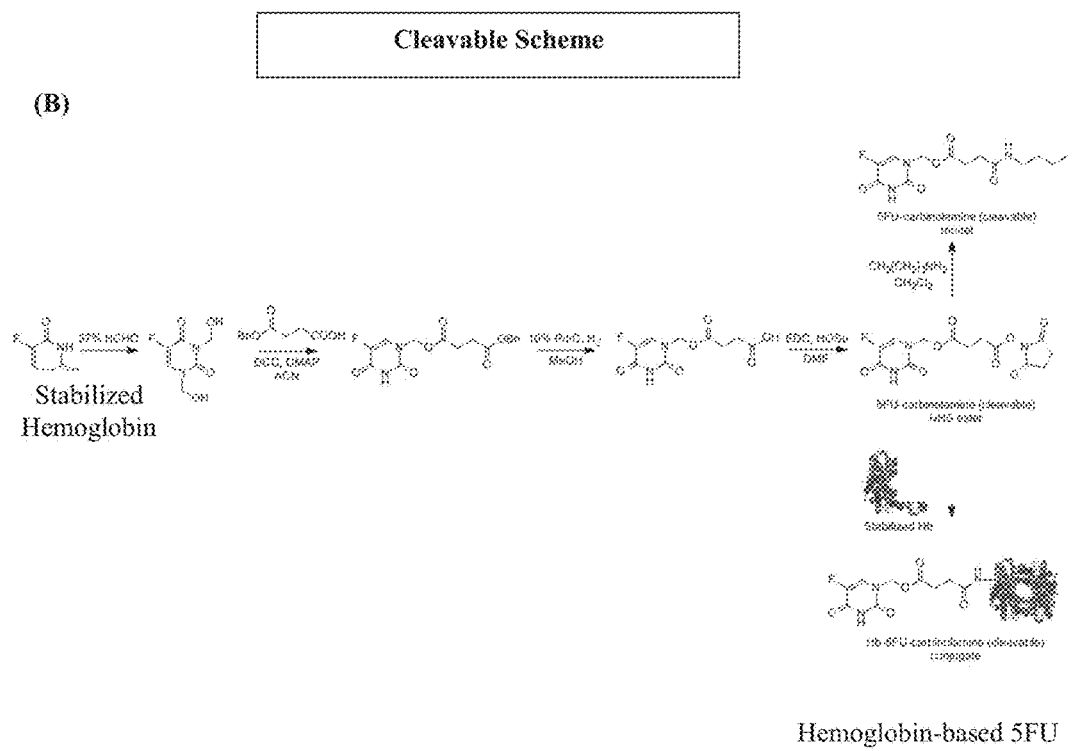
FIG. 4B shows the synthetic scheme Hb-5FU-carbinolamine (cleavable) conjugate.
Figure 5A:
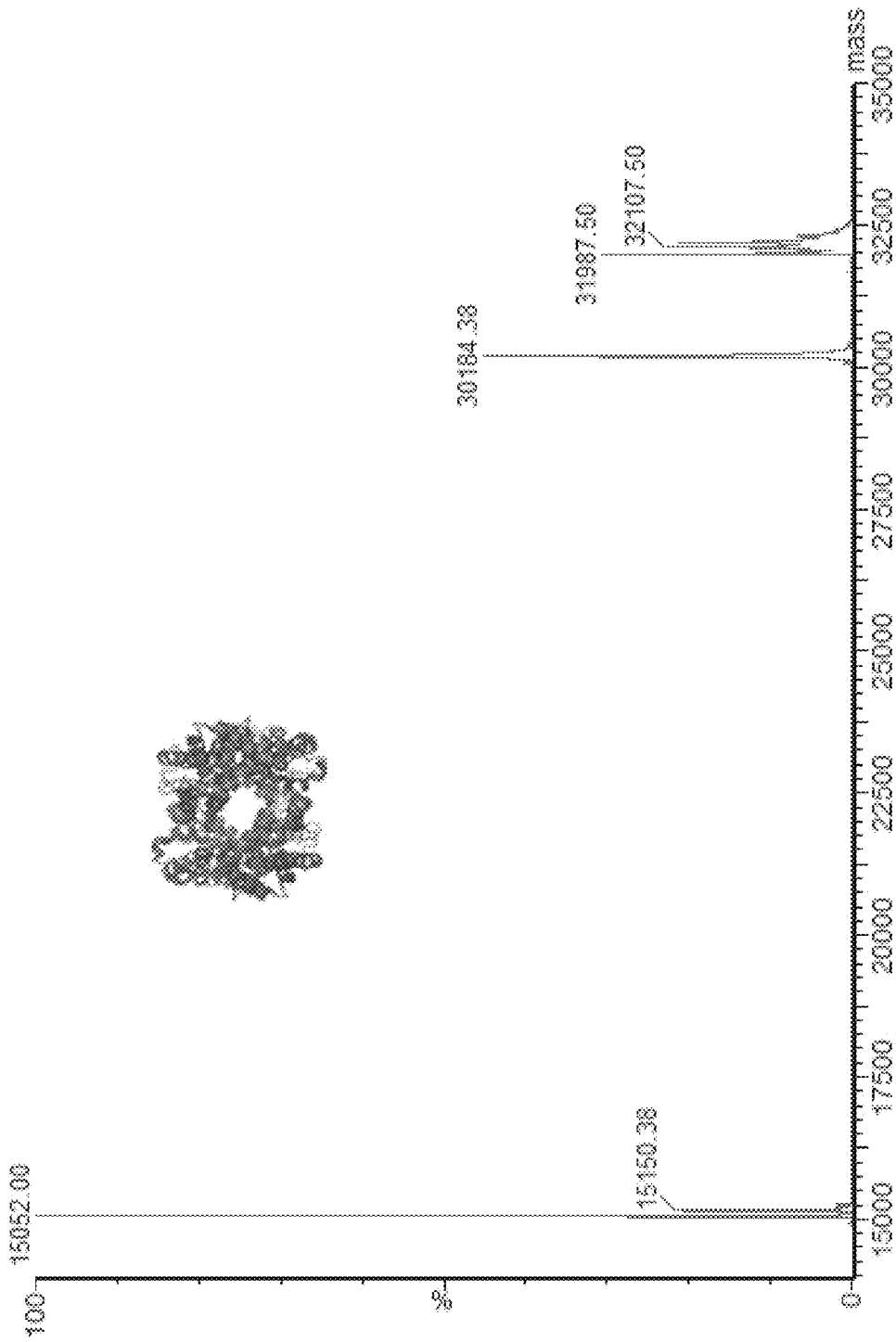
FIG. 5A shows the LC-MS results for stabilized hemoglobin.
Figure 5C:
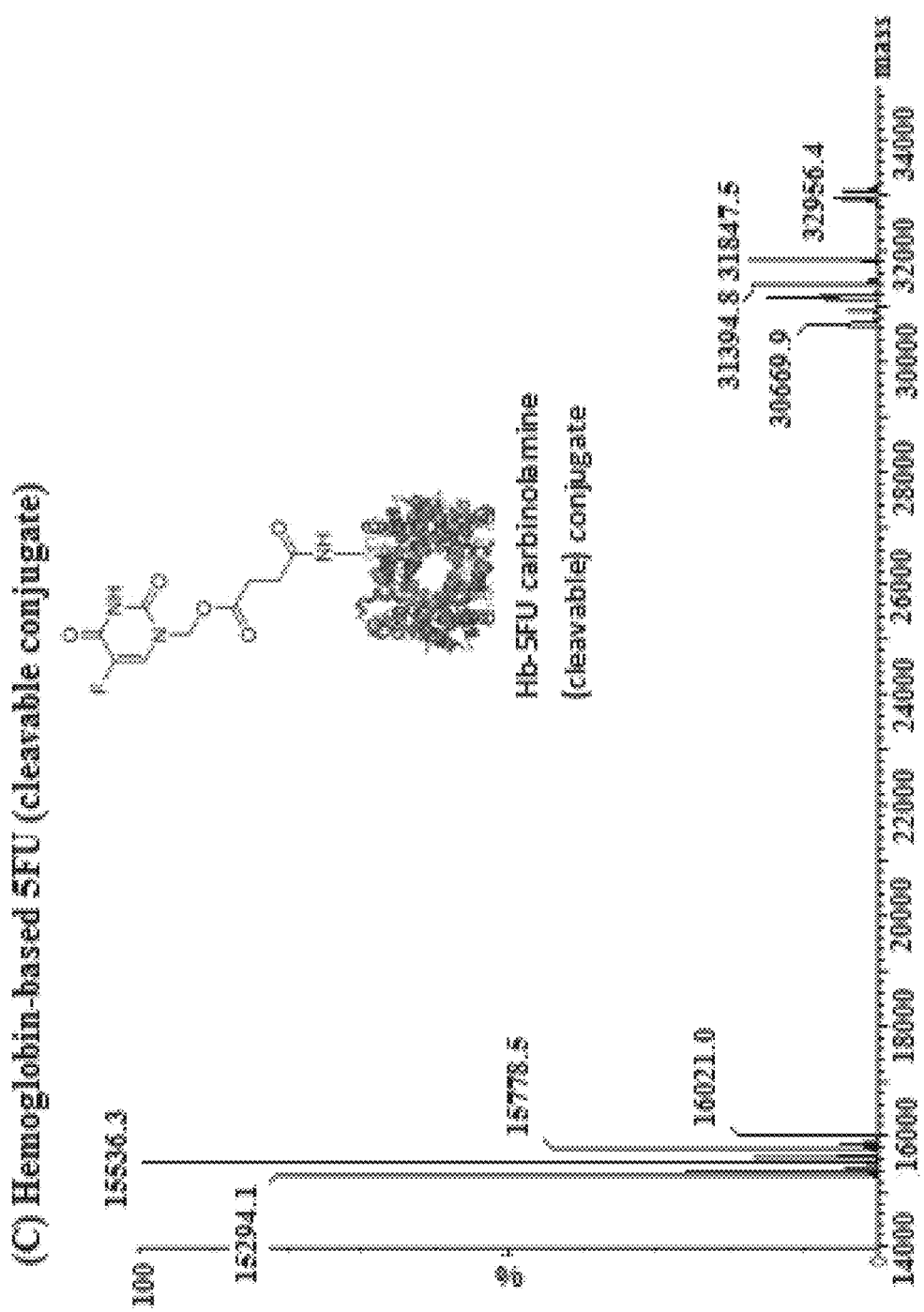
FIG. 5C shows the LC-MS results for Hb-5FU-carbinolamine (cleavable) conjugate.

The modified hemoglobin linked with 5FU (Hb-FU) using non-cleavable linker (non-cleavable conjugate) is shown in FIG. 4A and the modified hemoglobin linked with 5FU (Hb-FU) using cleavable linker (cleavable conjugate) is shown in FIG. 4B. It has been demonstrated successfully that the modified hemoglobin is linked to 5FU as shown in the LC-MS experiment. The mass of 5FU and Hb-FU are 130 Da and ~65 kDa respectively. A cleavable linker (e.g. carbinolamine, disulfide, carbamide, aminal, carbonate, ester, carbamate, phosphate, amide, acetal, imine, oxime, ether and sulfonamide groups) that can be cleaved under physiological conditions can be inserted between the hemoglobin moiety and the therapeutic moiety. A non-cleavable linker comprises alkyl and aryl groups linker can also be inserted between the hemoglobin moiety and the therapeutic moiety, which is not easily cleaved by hydrolysis and/or redox reaction. FIG. 5 shows the LC-MS result for (A) stabilized hemoglobin and (B) modified hemoglobin-based 5FU (non-cleavable conjugate) and (C) modified hemoglobin-based 5FU (cleavable conjugate). The pharmaceutical composition of the present invention contains the presently claimed hemoglobin-based therapeutic agent for targeting the cancer cells together with therapeutic effect in cancer treatment.

Figure 6A:
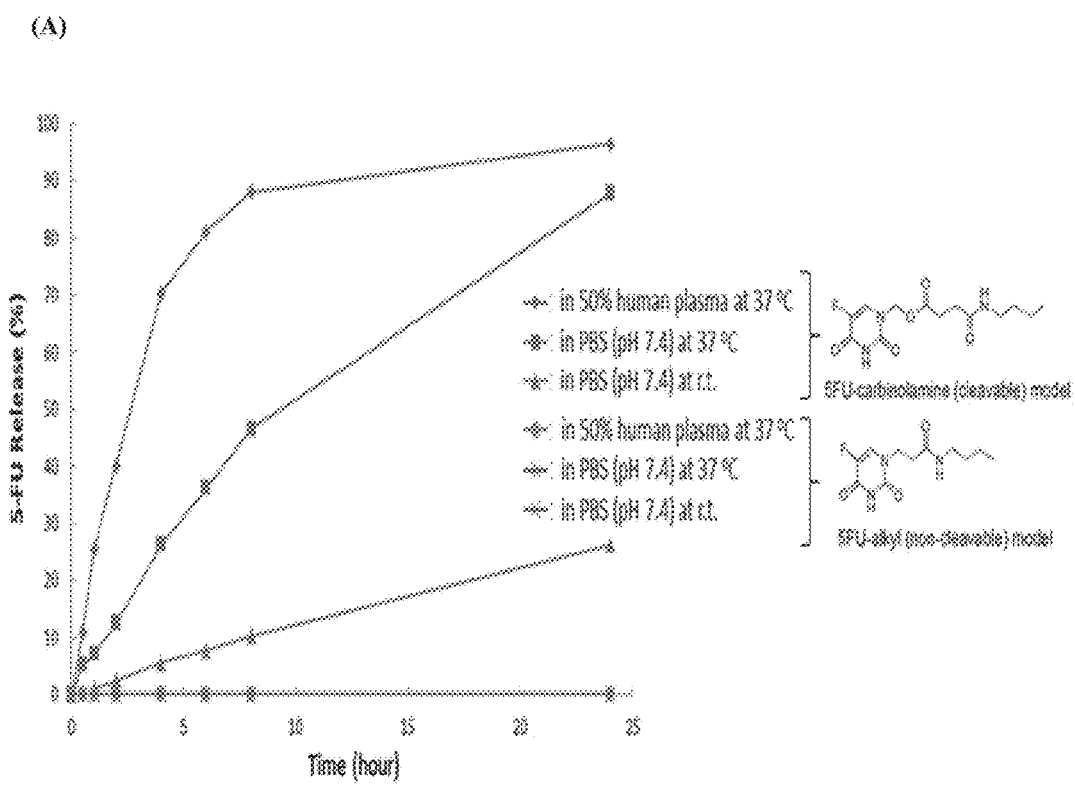
FIG. 6A shows the release of 5FU from 5FU-carbinolamine (cleavable) and 5FU-alkyl (non-cleavable) model in HPLC studies.

The release of 5FU from (A) 5FU-carbinolamine (cleavable) model and 5FU-alkyl (non-cleavable) model and (B) hemoglobin-based 5FU with cleavable linker (Hb-5FU carbinolamine conjugate) is shown in FIG. 6A and FIG. 6B respectively. The 5FU released from (FIG. 6A) 5FU-carbinolamine (cleavable) model and 5FU-alkyl (non-cleavable) model is performed in 50 mM phosphate buffer saline (pH 7.4), and 50% human plasma. A 100 µL of sample (10 µmol/mL DMSO) is placed into a 1.5 mL eppendorf tube containing 900 µL of either 50 mM phosphate buffer saline (pH 7.4), or 50% human plasma and is placed at room temperature (25° C.) or at 37° C. A 100 µL aliquot is withdrawn at various time points for HPLC analysis. From a solution of sample in 50% human plasma, aliquots are withdrawn and are then quenched with an equal volume of THF and vortexed for 1 min After centrifugation at 3200 r.p.m. for 2 min, an aliquot of supernatant is pipetted and analyzed by HPLC. The 5FU released from (FIG. 6B) hemoglobin-based 5FU with cleavable linker (Hb-5FU-carbinolamine (cleavable) conjugate) is performed in DB buffer (pH 7.4), and 50% human plasma and analyzed by HPLC.

Decomposition of 5FU-carbinolamine (cleavable) model is observed under the following conditions with the rate in descending order: 50% human plasma at 37° C.>PBS (pH 7.4) at 37° C.>PBS (pH 7.4) at room temperature (room temperature, 25° C.). The 5FU-alkyl (non-cleavable) model is stable under any of these conditions.

Decomposition of hemoglobin-based 5FU with cleavable linker (Hb-5FU carbinolamine (cleavable) conjugate) is observed under the following conditions with the rate in descending order: 50% human plasma at 37° C.>DB buffer (pH 7.4) at 37° C.

Figure 7:
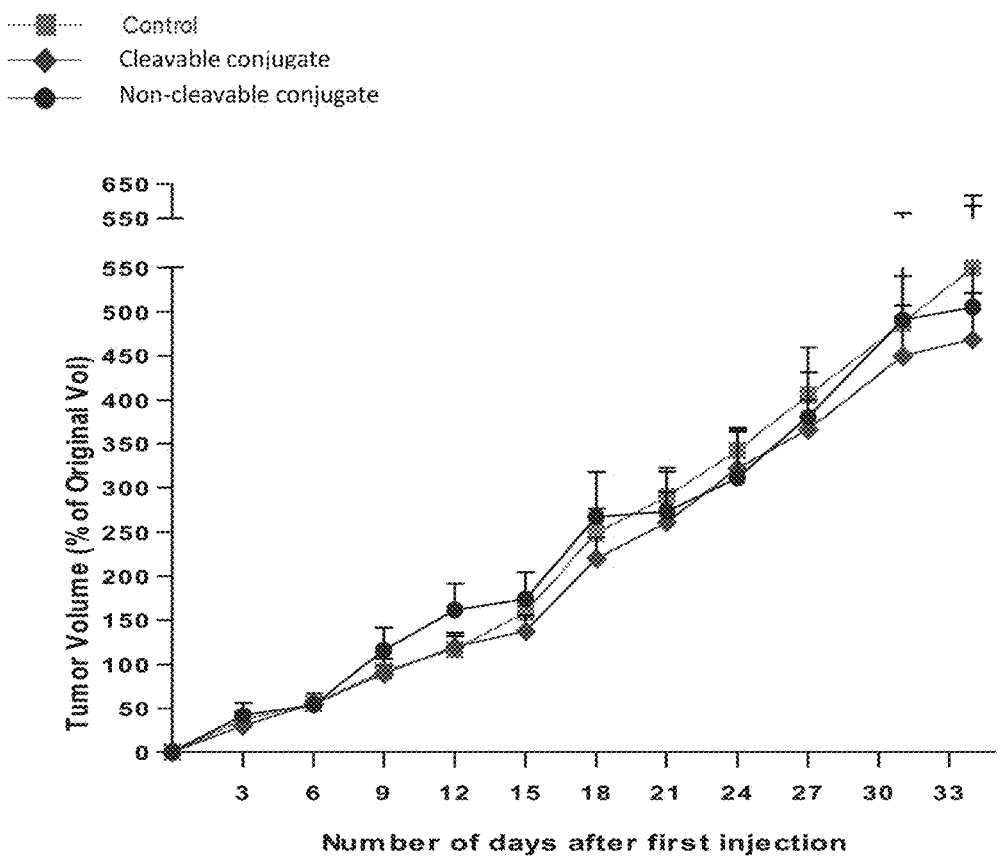
FIG. 7 shows the efficacy (Tumor Size) of hemoglobin-based 5FU in pancreatic cancer Capan-1 animal model.
Figure 8:
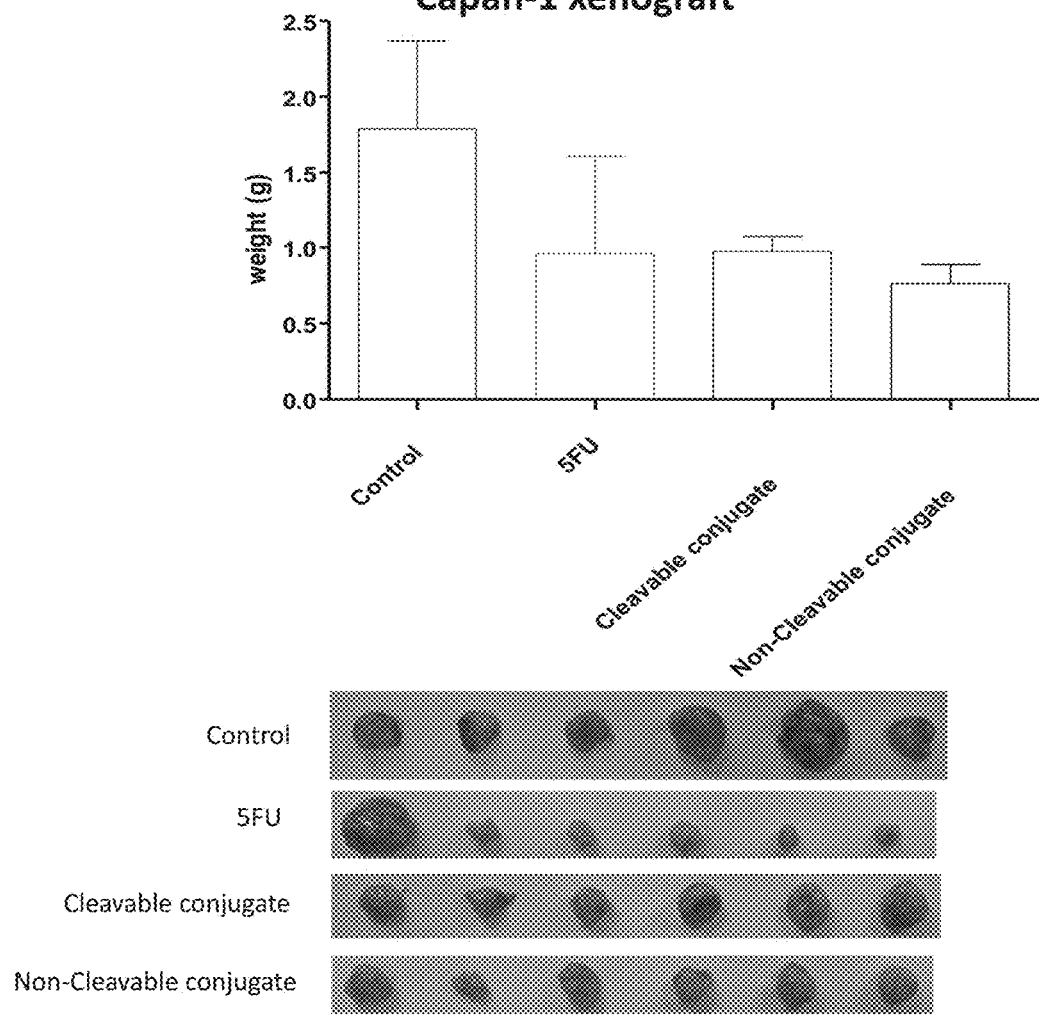
FIG. 8 shows the efficacy (Tumor Weight) of hemoglobin-based 5FU in pancreatic cancer Capan-1 animal model.
Figure 9:
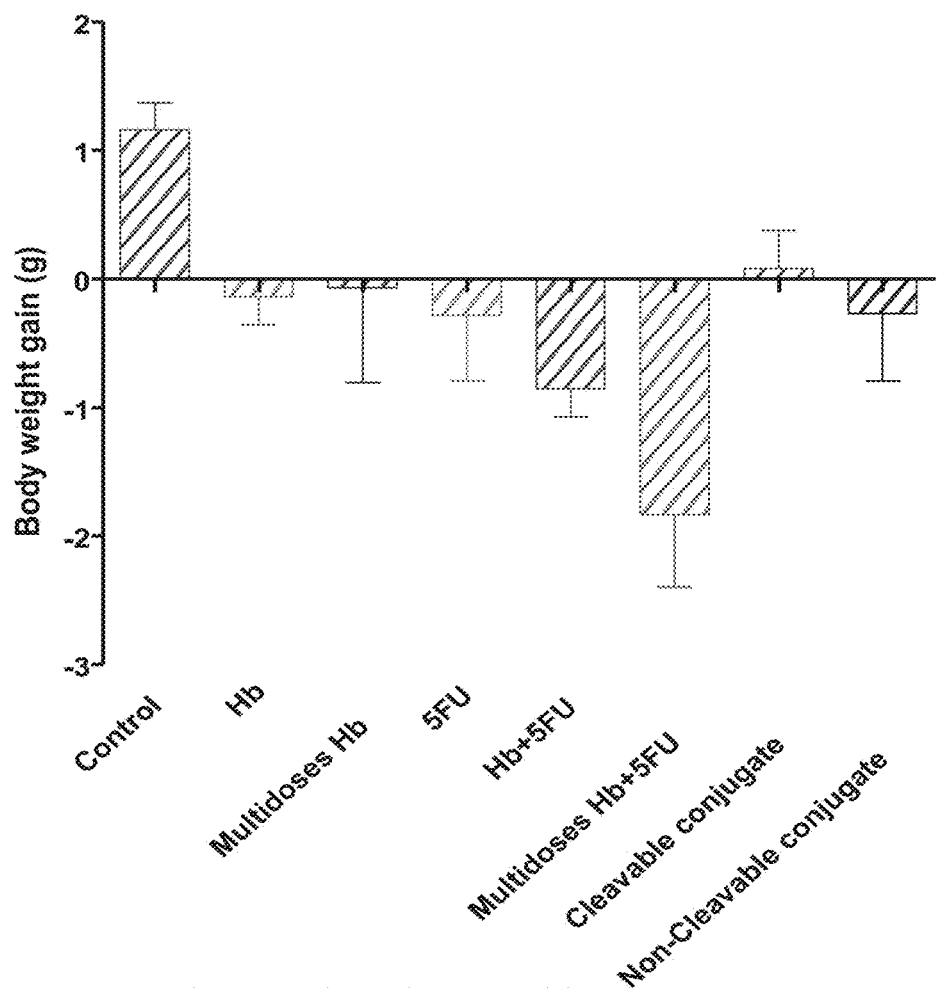
FIG. 9 shows the weight gain of the animal model (mice) carrying Capan-1 xenograft after drug treatment.
Figure 10:
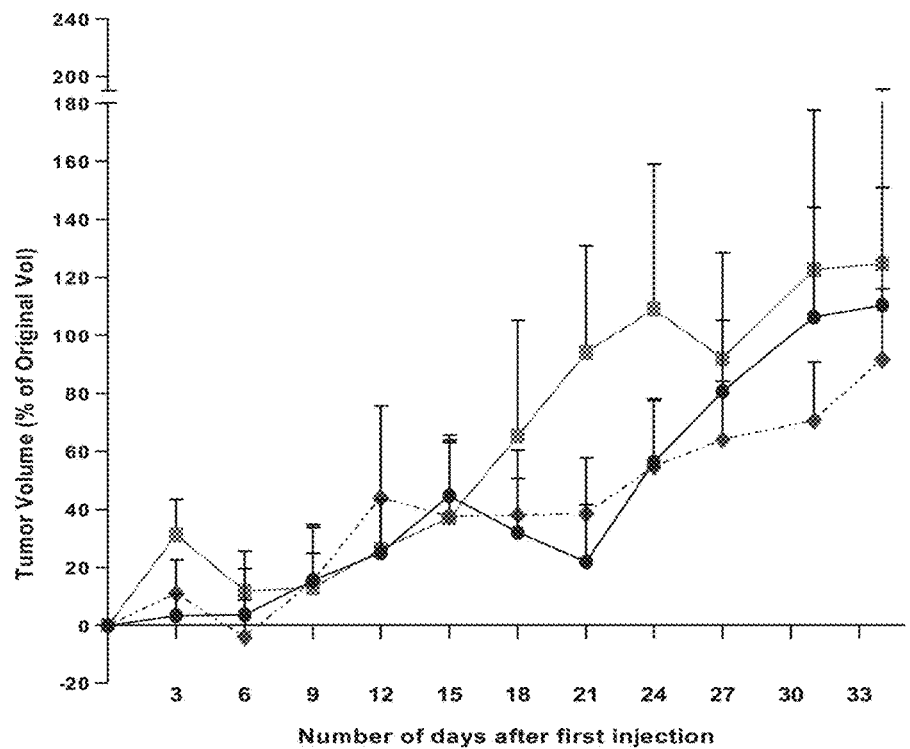
FIG. 10 shows the efficacy (Tumor Size) of hemoglobin-based 5FU in liver cancer SMMC7221 animal model.
Figure 11:
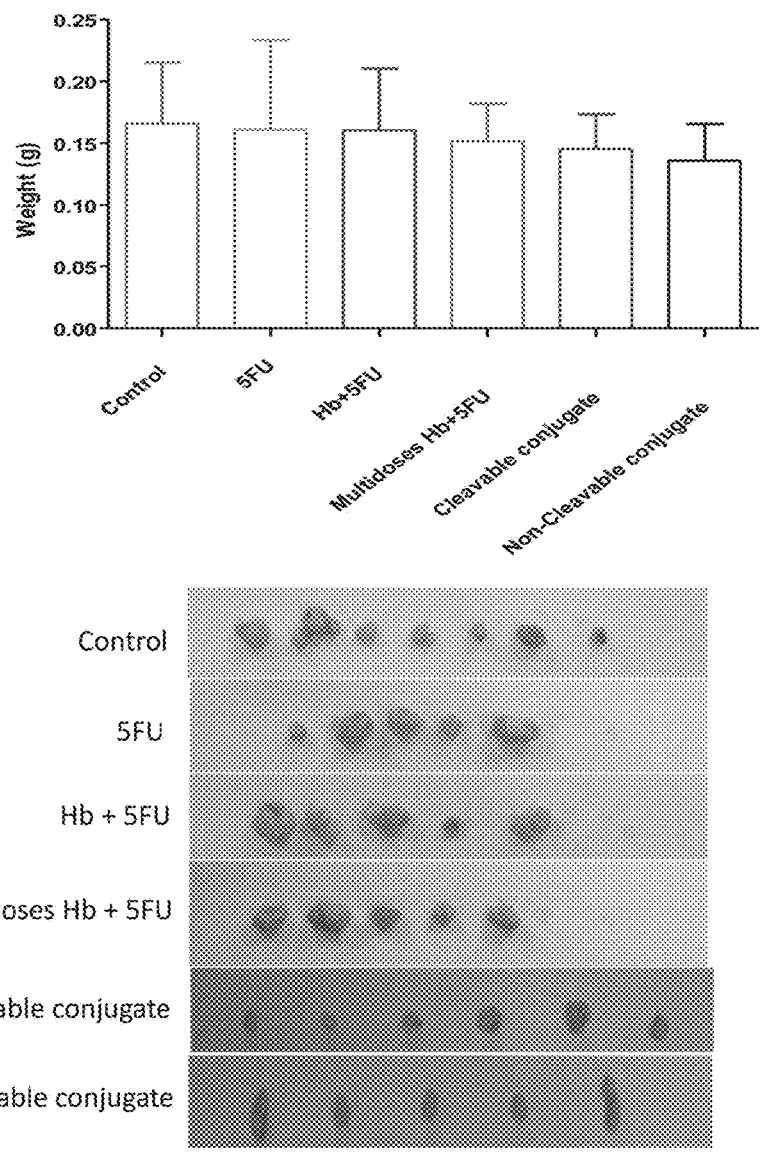
FIG. 11 shows the efficacy (Tumor Weight) of hemoglobin-based 5FU in liver cancer SMMC7221 animal model.
Figure 12:
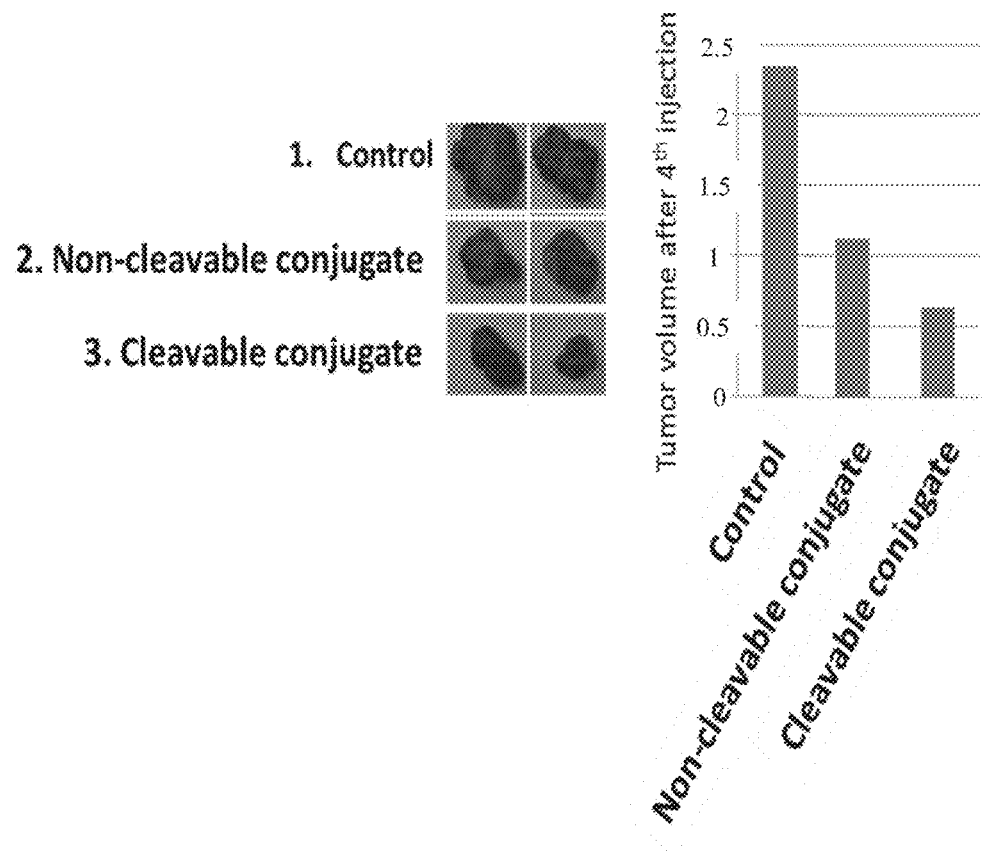
FIG. 12 shows the efficacy (Tumor Size) of hemoglobin-based 5FU in CD133+ liver cancer progenitor/Cancer-stem like cells HepG2 animal model.
Figure 13:
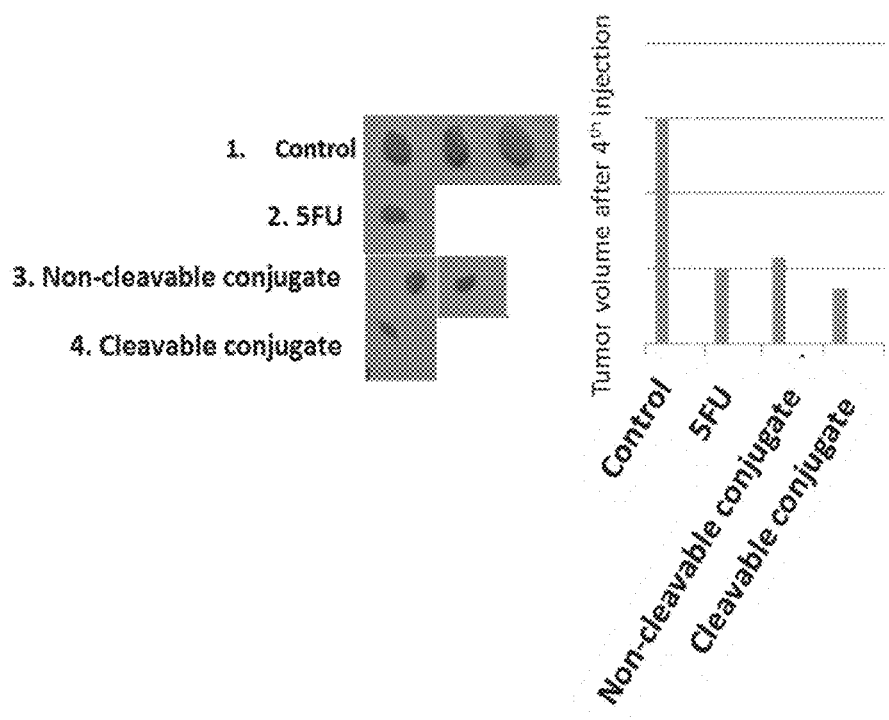
FIG. 13 shows the efficacy (Tumor Size) of hemoglobin-based 5FU in CD44+CD24− breast cancer progenitor/Cancer-stem like cells MCF7 animal model.

The pharmaceutical composition of the present invention contains hemoglobin-based therapeutic agent targeting the cancer cells with therapeutic effect for cancer treatment. Our animal studies reveal suppression of tumor growth in hemoglobin based 5FU-treated mice in Pancreatic cancer xenograft (Capan-1) by 20-22% in tumor volume (FIG. 7), and by 130% in tumor weight (FIG. 8). No significant weight loss can be observed after the 28 day treatment period (FIG. 9), suggesting that hemoglobin based 5FU is not cytotoxic. Similar trend can be observed in the suppression on tumor growth in hemoglobin based 5FU-treated mice in Liver cancer xenograft (SMMC7221) by 38% in tumor volume (FIG. 10), and by 33% in tumor weight (FIG. 11). Our animal studies reveal significant suppression on tumor growth in hemoglobin based 5FU-treated mice engrafted with liver cancer CD133+ stem-like cells or breast cancer CD44+/CD24− stem-like cells. Suppression on tumor growth, 188% in CD133+ LCSC xenografts (FIG. 12) 200% in CD44+CD24− BCSC xenografts (FIG. 13) and are detected respectively.

Figure 14:
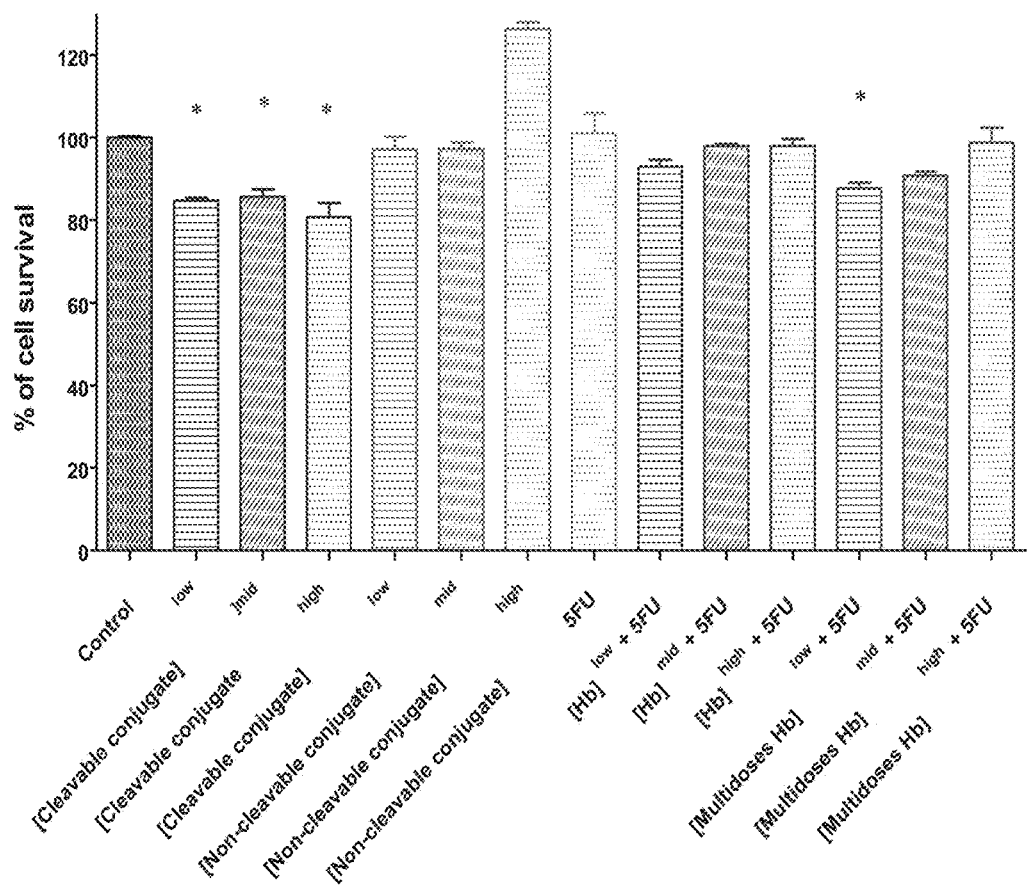
FIG. 14 shows the efficacy (Cytotoxicity) of hemoglobin-based 5FU in HCT116 colon cancer in vitro.
Figure 15:
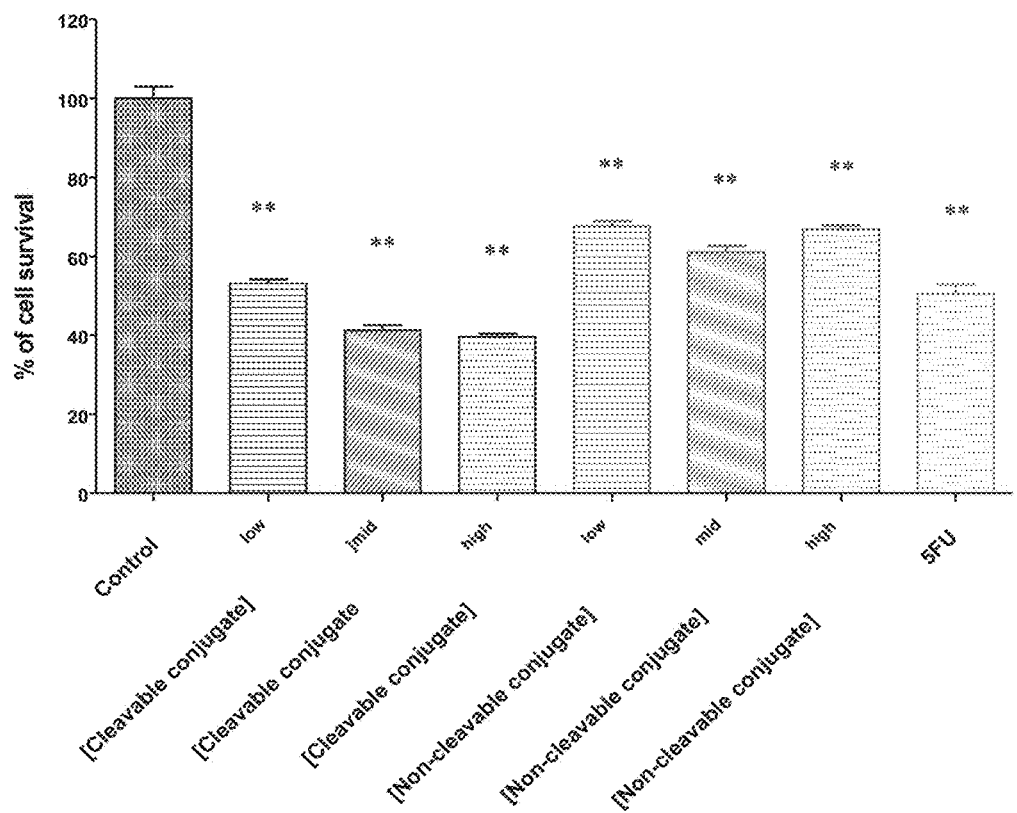
FIG. 15 shows the efficacy (Cytotoxicity) of hemoglobin-based 5FU in HCT460 Non-small cell Lung cancer in vitro.
Figure 16:
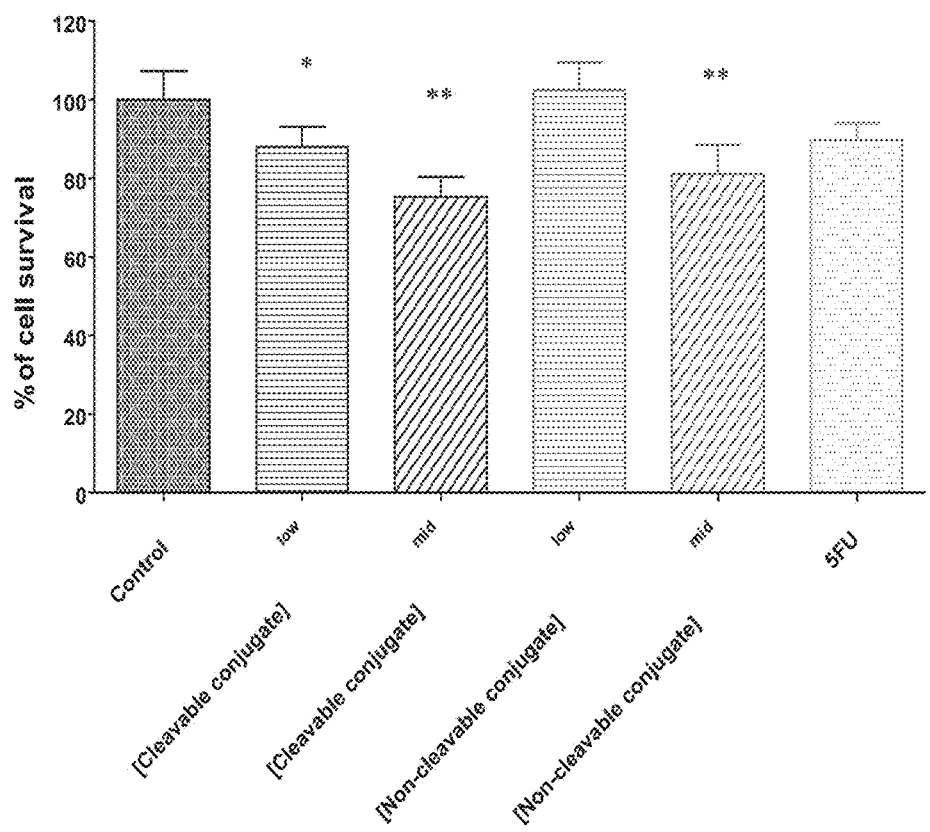
FIG. 16 shows the efficacy (Cytotoxicity) of hemoglobin-based 5FU in HL60 Acute leukemia in vitro.
Figure 17:
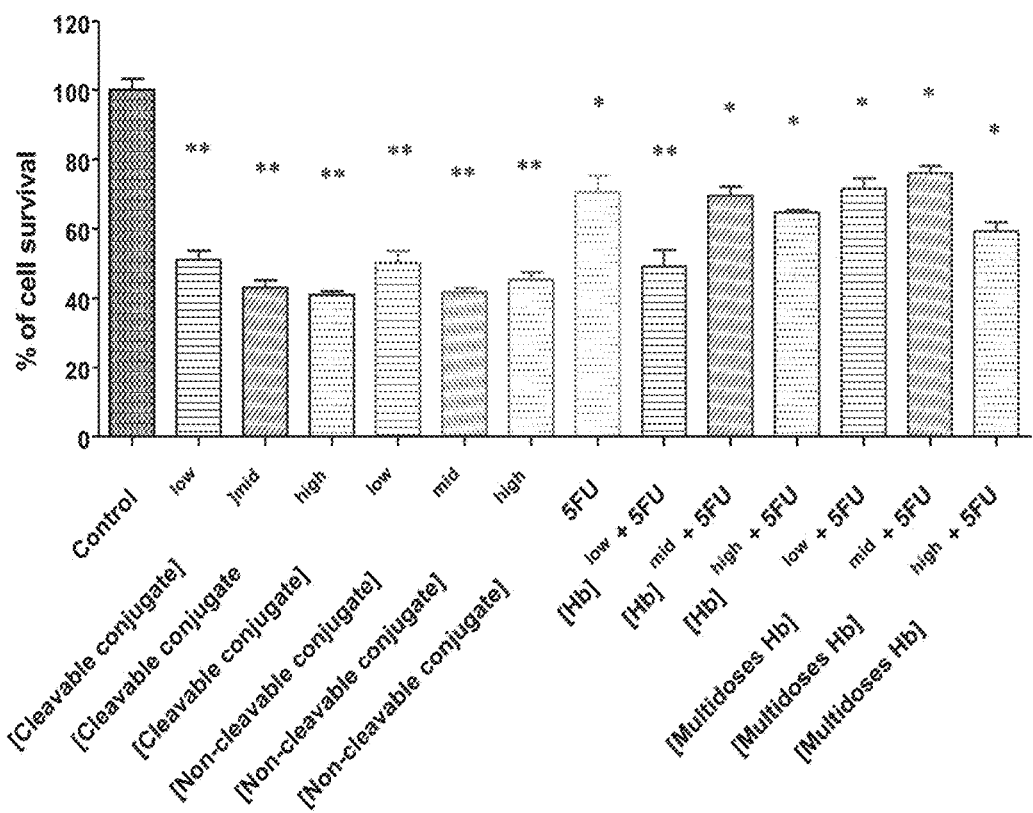
FIG. 17 shows the efficacy (Cytotoxicity) of hemoglobin-based 5FU in A172 brain cancer in vitro.
Figure 18:
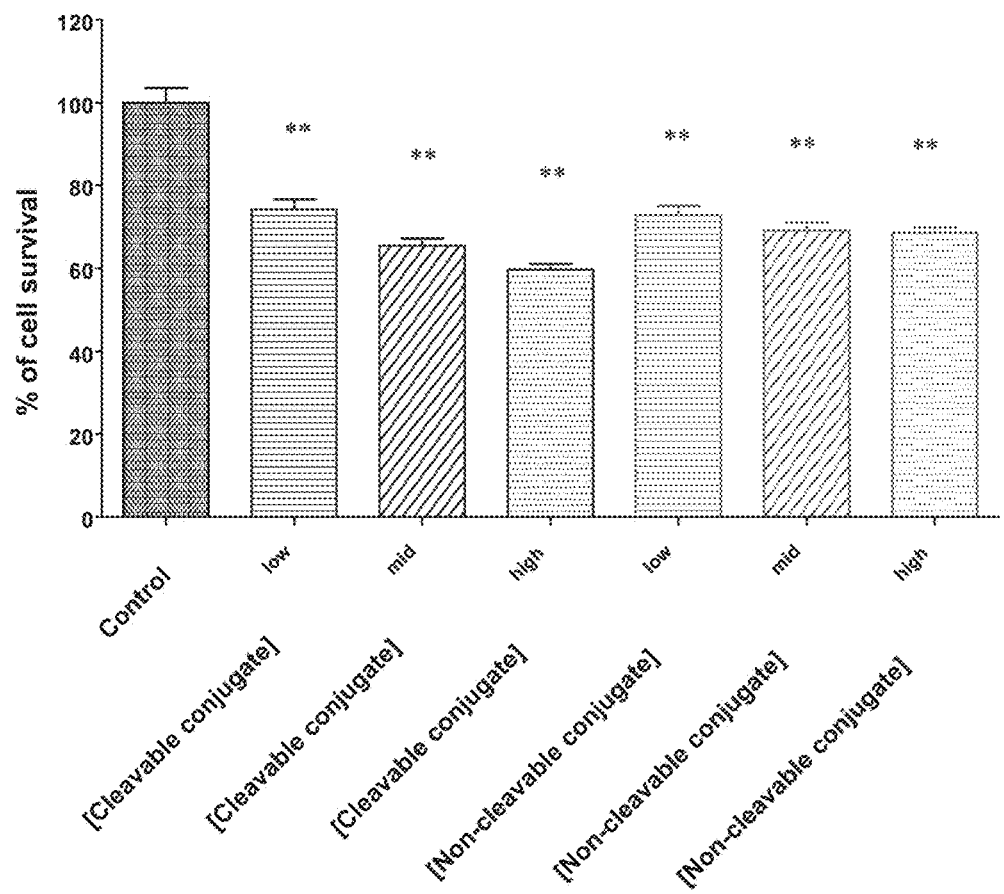
FIG. 18 shows the efficacy (Cytotoxicity) of hemoglobin-based 5FU in breast cancer in vitro.
Figure 19:
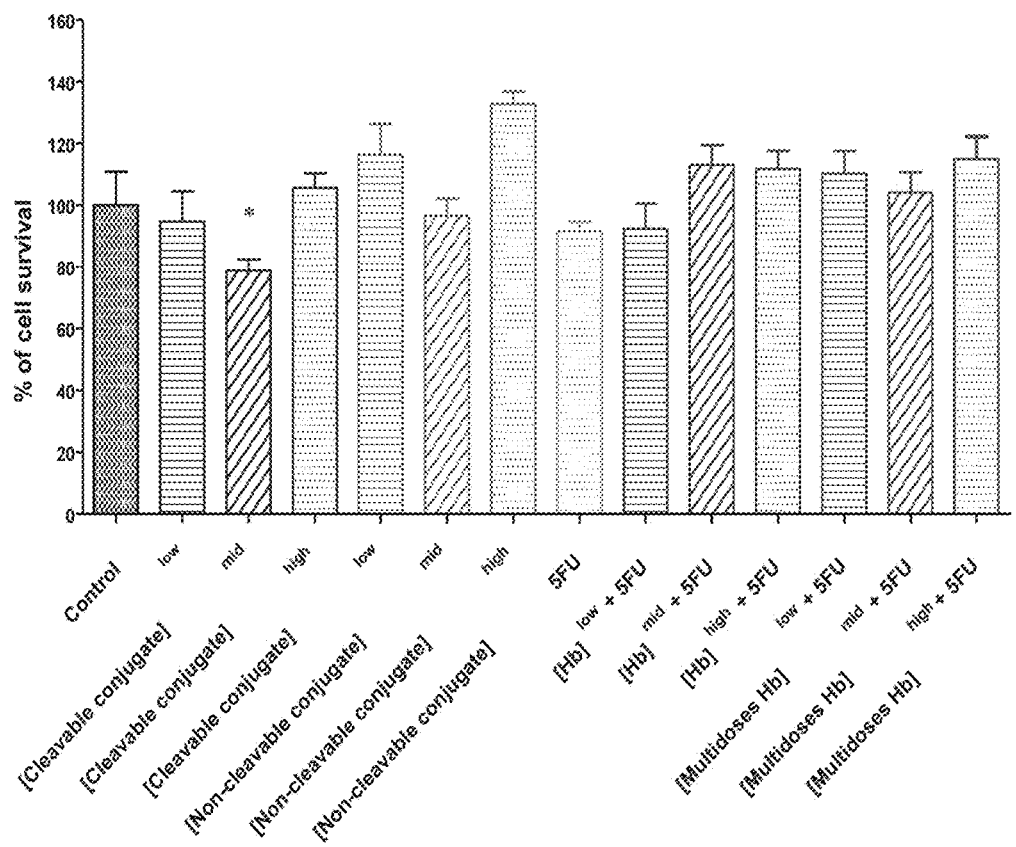
FIG. 19 shows the efficacy (Cytotoxicity) of hemoglobin-based 5FU in breast cancer in vitro.

The captioned hemoglobin based 5FU's ability in targeting other cancer cells are exemplified in various in vitro models. By employing the MTT assay, cytotoxicity of hemoglobin based 5FU on various cancer cells are determined: 20% cell death in HCT116 colorectal carcinoma (FIG. 14), 60% in H460 Non-small cell lung cancer cells (FIG. 15), 28% in Jurket Leukemic cells (FIG. 16), 57% in A172 Glioblastoma brain cancer cells (FIG. 17), 35% in MCF7 breast cancer cells (FIG. 18), and 20% in Huh7 liver cancer cells respectively (FIG. 19).

Figure 20:
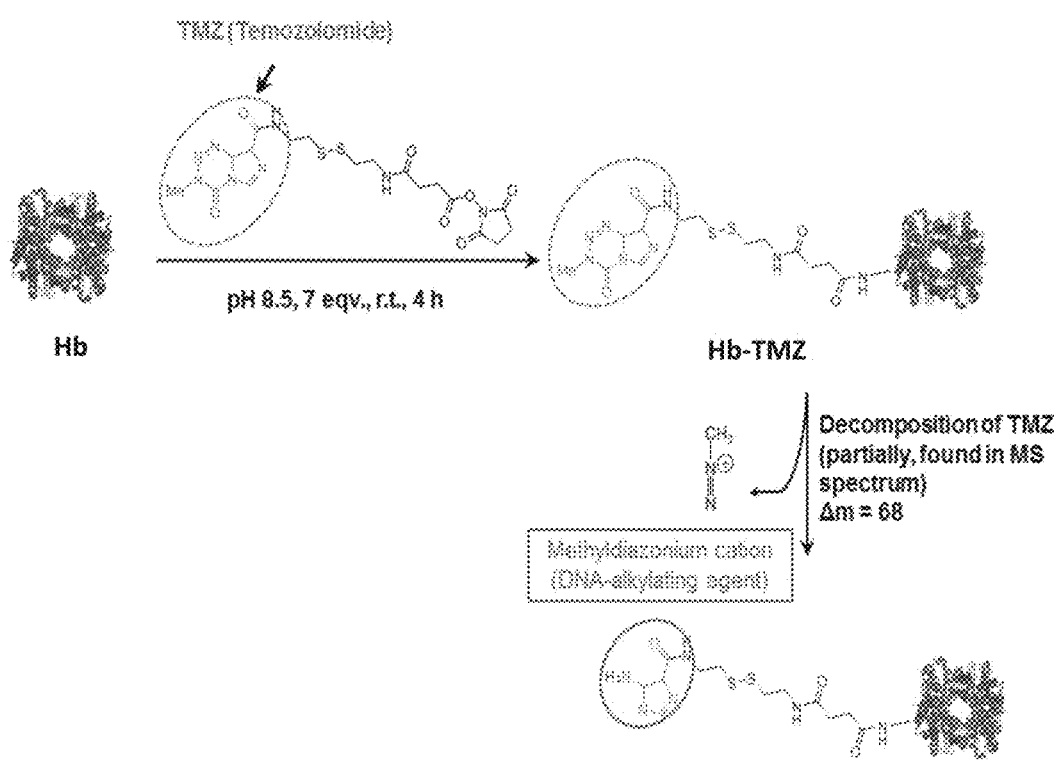
FIG. 20 shows the structure of Temozolomide (TMZ) and the modified hemoglobin linked with TMZ.
Figure 21:
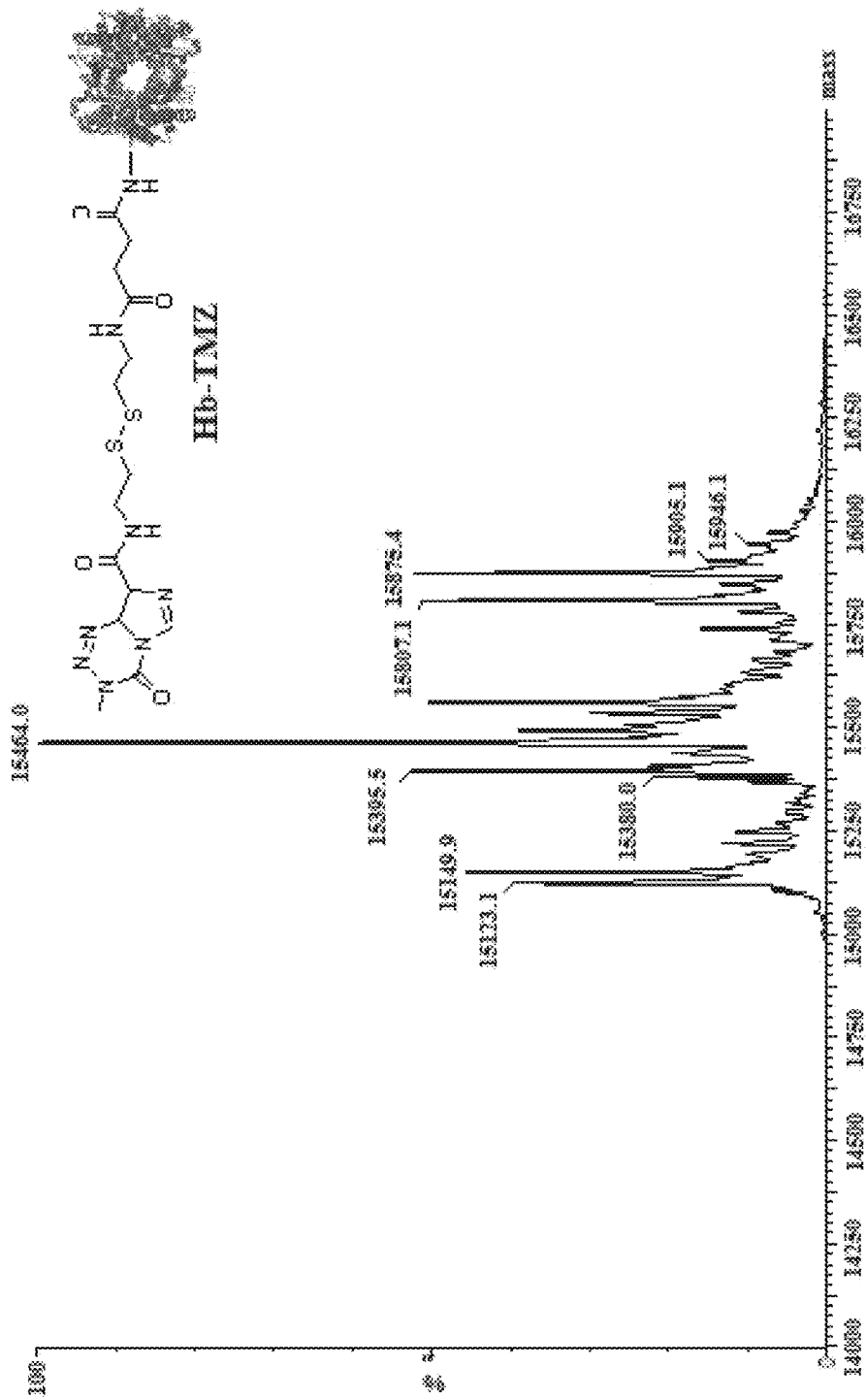
FIG. 21 shows the LC-MS results for hemoglobin-based TMZ.

The structure of temozolomide (TMZ) and the modified hemoglobin linked with TMZ are shown in FIG. 20. It has been demonstrated successfully that the modified hemoglobin is linked to TMZ as shown in a LC-MS experiment. FIG. 21 shows the LC-MS result for the present hemoglobin based TMZ.

Figure 22:
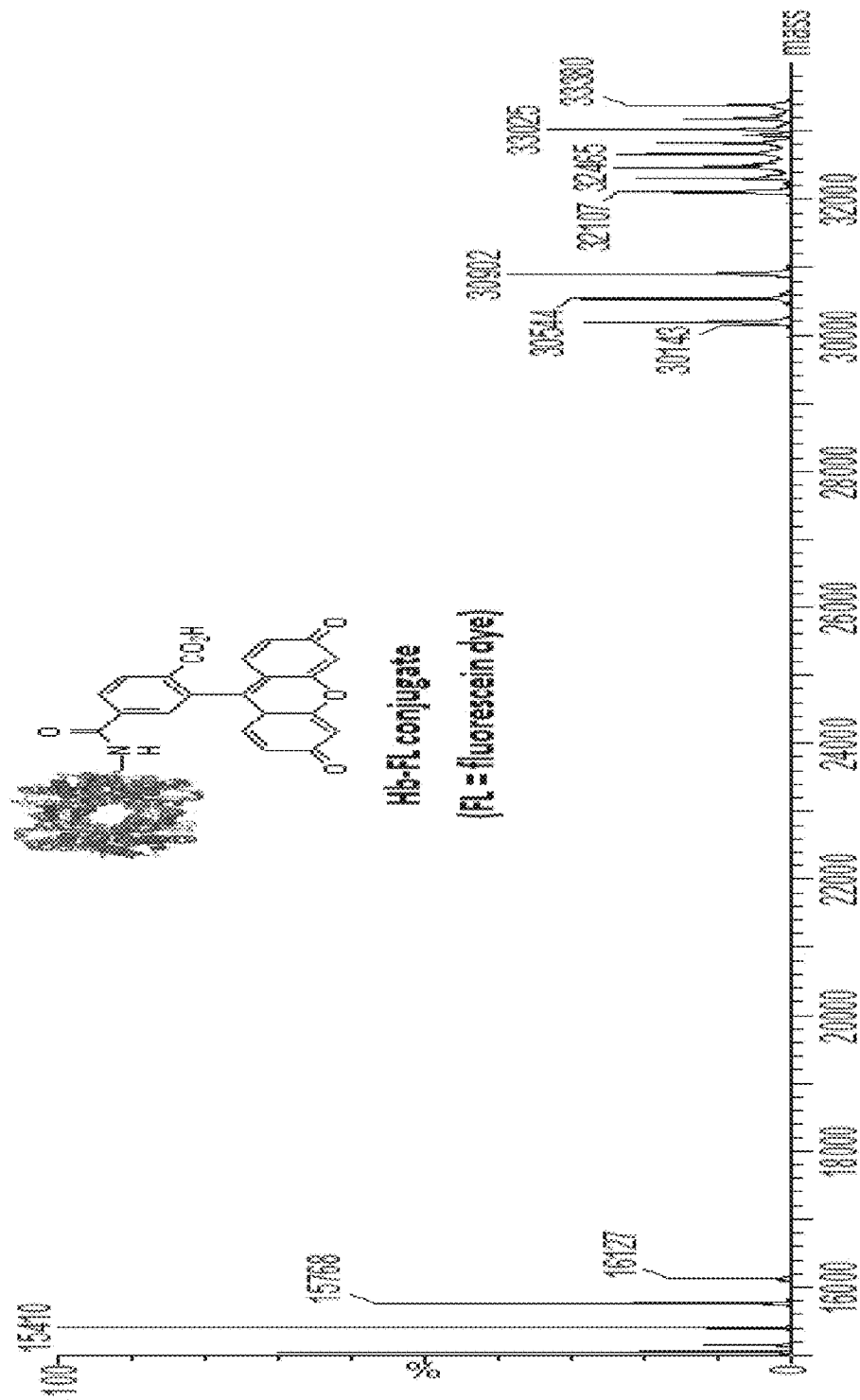
FIG. 22 illustrates that one or more molecules of fluorescein can be linked to one molecule of hemoglobin.
Figure 23A:
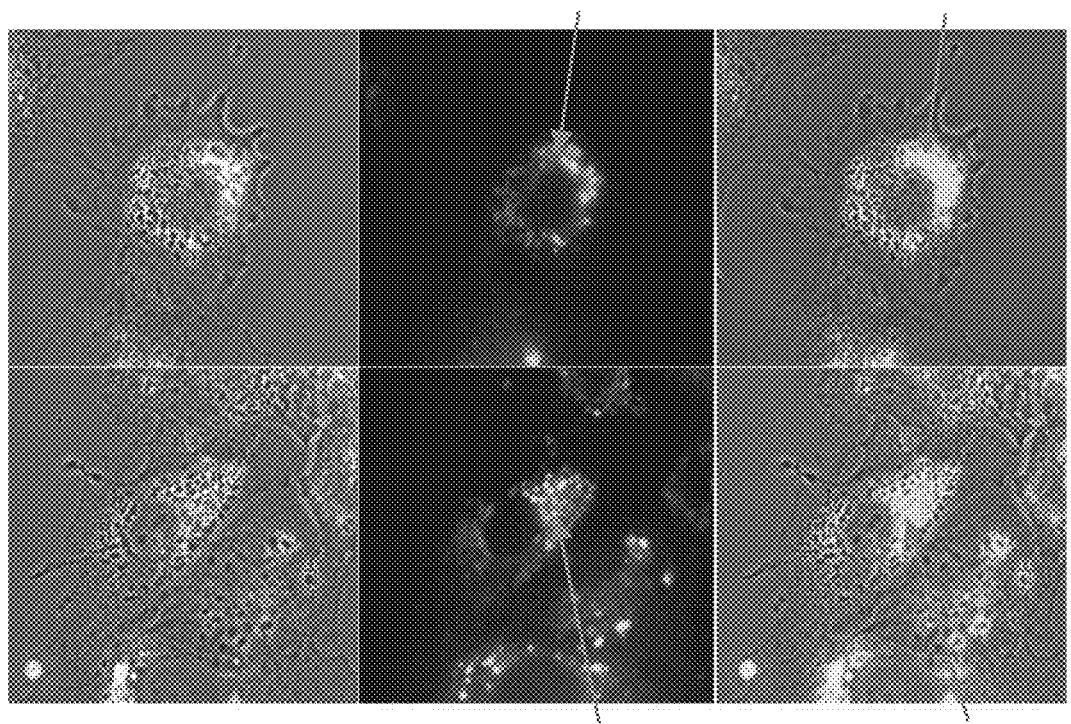
FIG. 23A illustrates that the fluorescent labeled modified hemoglobin can enter into liver cancer cells successfully. Arrow indicates where the fluorescent signal (single or double fluorescent labeled) is detected from the cells under the microscope using different filter(s) of the microscope.
Figure 23B:
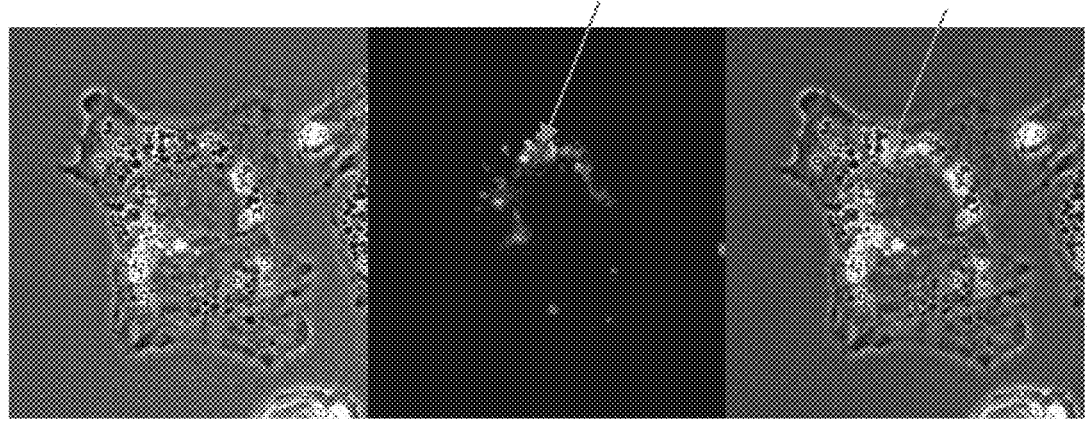
FIG. 23B illustrates that the Hb-5FU-alkyl(non-cleavable)-FL conjugate labeled with one fluorescent dye can enter into liver cancer cells successfully. Arrow indicates where the fluorescent signal (single or double fluorescent labeled) is detected from the cells under the microscope using different filter(s) of the microscope.

FIG. 22 illustrates that more than one molecule of fluorescein (e.g. fluorescein 6-carboxysuccinimidyl ester, F-6-NHS) can be linked to a molecule of hemoglobin. The fluorescent labeled hemoglobin can also enter into the cancer cells (e.g., liver cancer cells) and the result is illustrated in FIG. 23A. It is expected that the modified hemoglobin-based therapeutic agent can also kill the cancer cells effectively. A live cell imaging is employed in the present application to clearly document how various forms of modified hemoglobin based 5FU could be uptaken into the cancer cells (FIG. 23A, 23B). Liver cancer cells, HepG2, and CD133+ liver cancer stem-like cells are exposed to 0.0125 g/dL for 15 min prior to live cell acquisition. Modified hemoglobin based 5FU is observed to be uptaken into the cytoplasm of the cancer cells after 15 min of exposure. The uptake peaks after 1 h of exposure is also observed.

Figure 24:
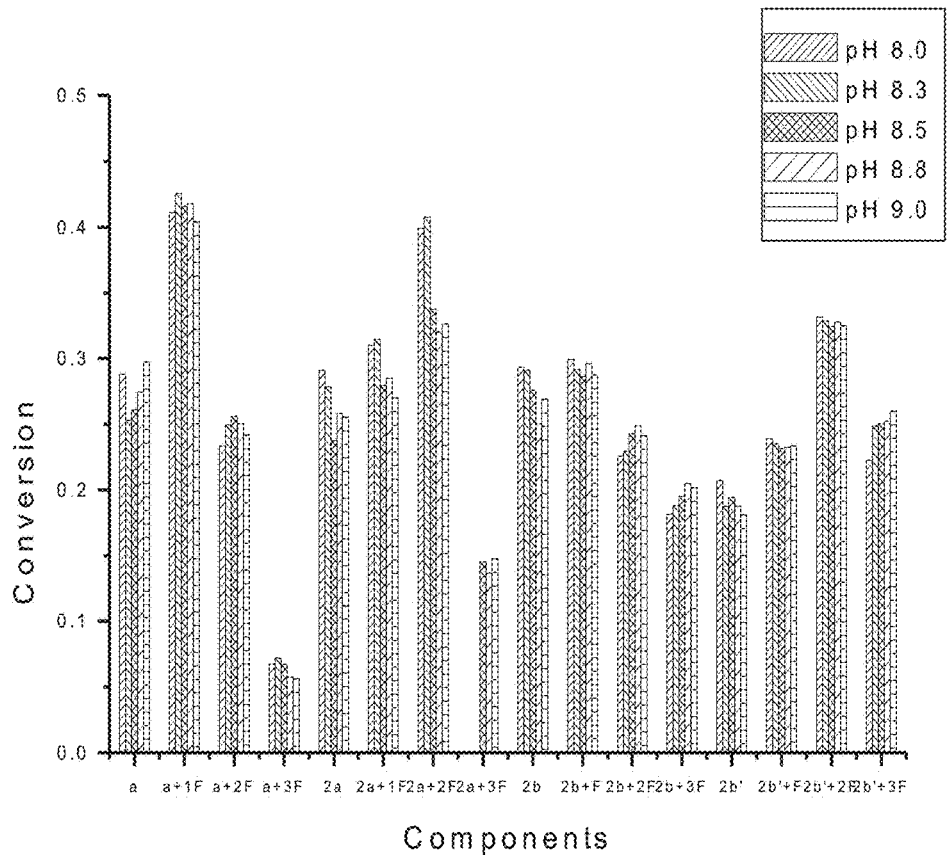
FIG. 24 shows the conversion of each unit of fluorescein 6-carboxysuccinimidyl ester (F-6-NHS) modified hemoglobin under different pH (pH 8.0, 8.3, 8.5, 8.8 and 9).
Figure 25:
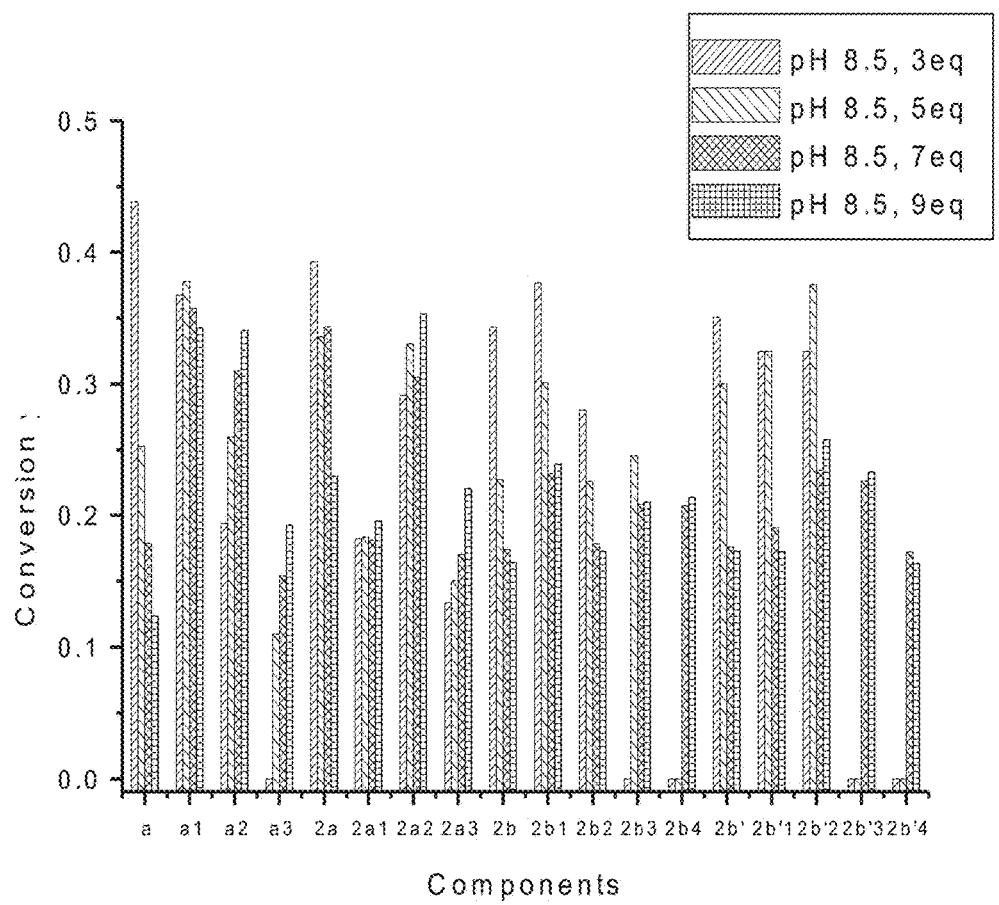
FIG. 25 shows the conversion of each unit of F-6-NHS-modified hemoglobin under different ratios of F-6-NHS (3, 5, 7 and 9 equivalents) to hemoglobin at pH 8.5.
Figure 26:
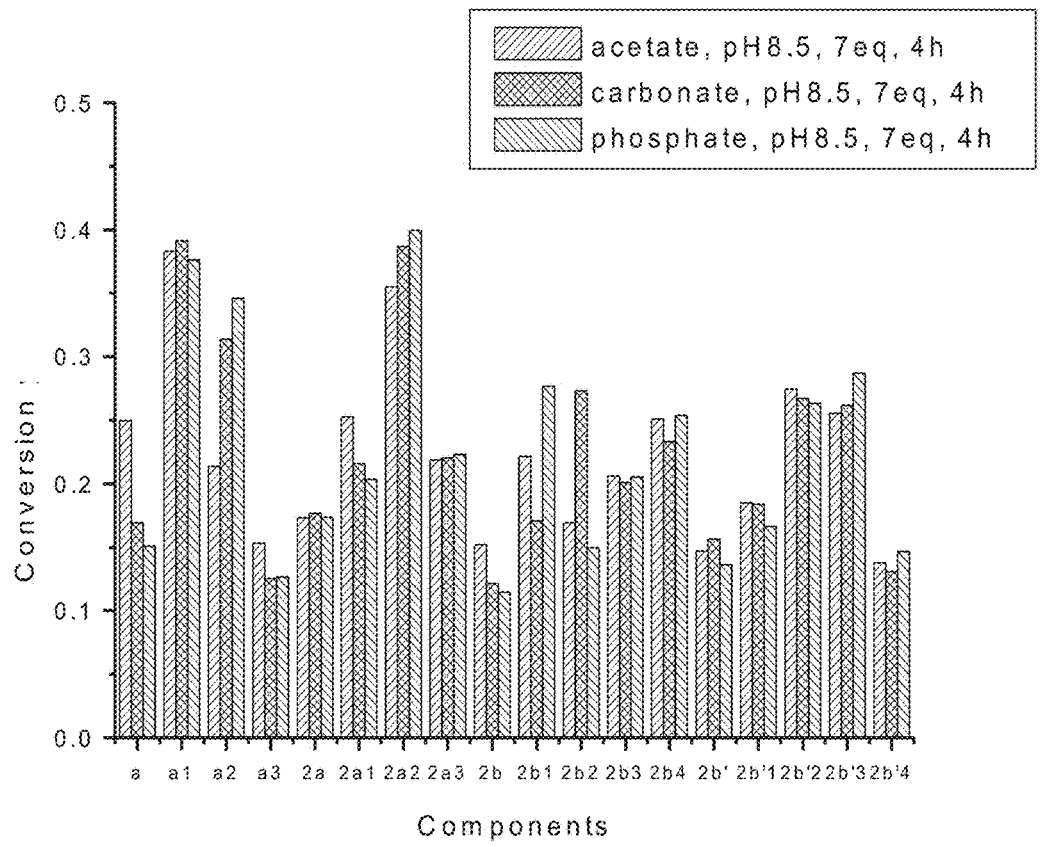
FIG. 26 shows the conversion of each unit of F-6-NHS-modified hemoglobin with 7 equivalents of F-6-NHS to modified hemoglobin in different buffers (acetate, carbonate and phosphate) at pH 8.5.

The condition for modification of hemoglobin by F-6-NHS is optimized for different parameters including pH, mole ratio and buffer. FIG. 24 shows the conversion of each unit of F-6-NHS-modified hemoglobin under different pH (pH 8.0, 8.3, 8.5, 8.8 and 9.0). The preferred condition for chemical modification of stabilized hemoglobin is at pH 8.5. FIG. 25 shows the conversion of each unit of F-6-NHS-modified hemoglobin under different ratios of F-6-NHS to 1 equivalent of hemoglobin (3, 5, 7 and 9 equivalents) at pH 8.5. The preferred ratio between F-6-NHS and stabilized hemoglobin is 7:1. FIG. 26 shows the conversion of each unit of F-6-NHS-modified hemoglobin with F-6-NHS to hemoglobin (7:1 equivalents) in different buffers (acetate, carbonate and phosphate) at pH 8.5. There is no significant difference on the conversion under different buffer conditions.

Figure 27:
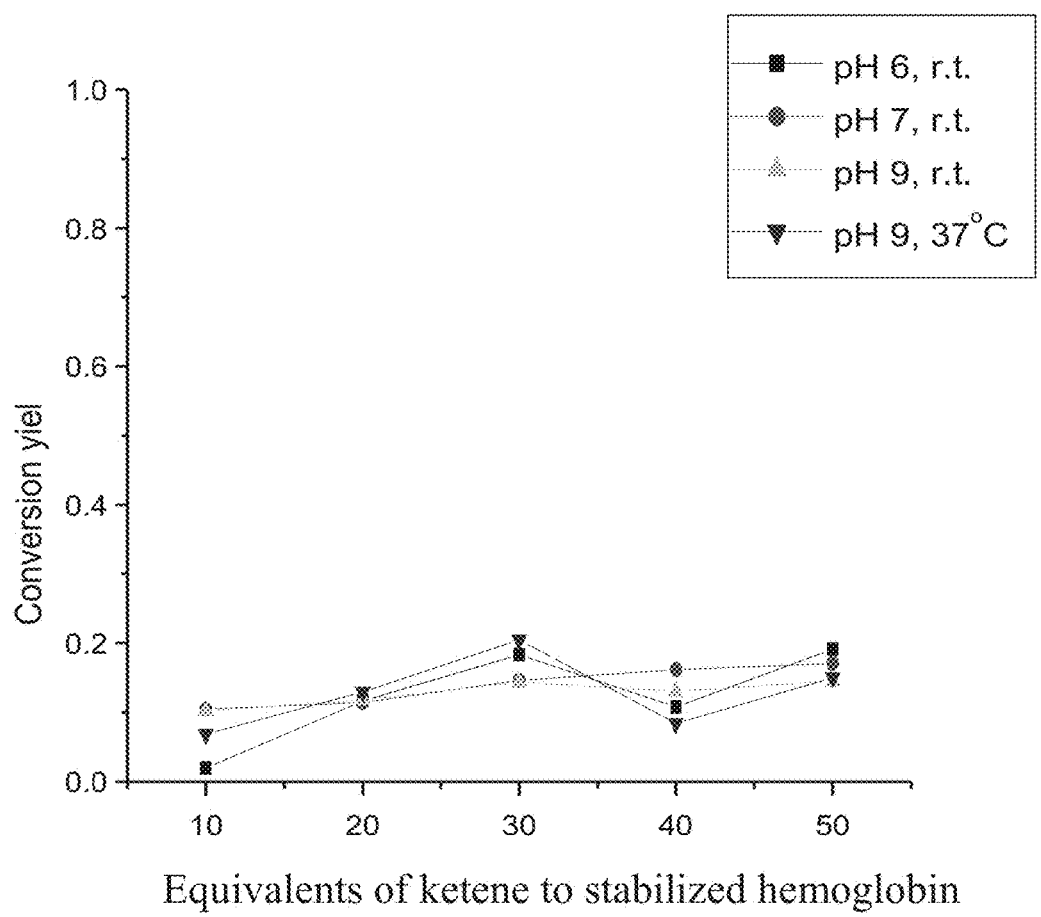
FIG. 27 shows the conversion of ketene-modified hemoglobin under different conditions.

The condition for modification of hemoglobin by ketene is optimized for different parameters including pH, temperature and mole ratio. FIG. 27 shows the conversion for ketene-modified hemoglobin under different conditions. The preferred condition is at pH 9, 37° C. and 30 equivalents.

Figure 28:
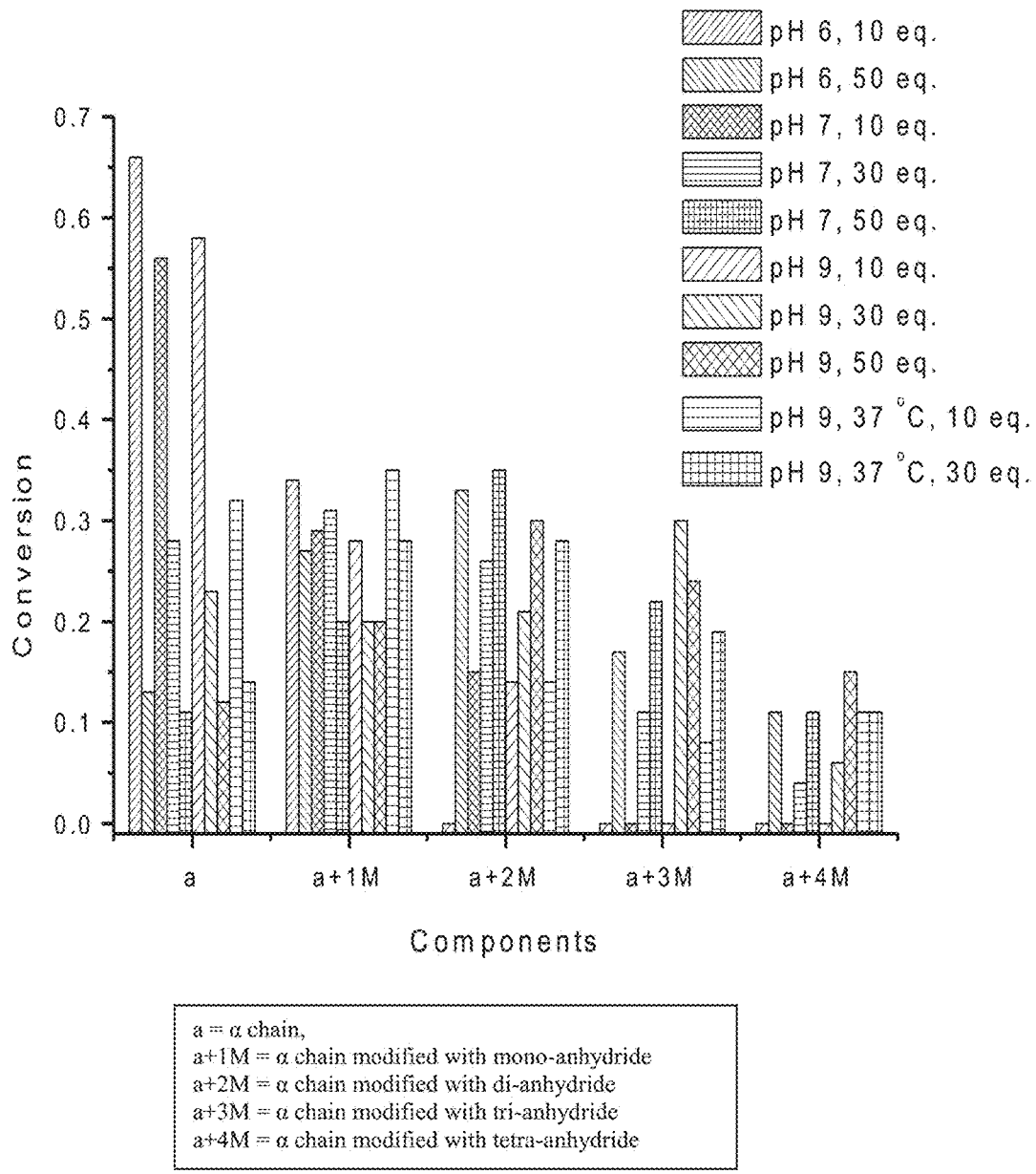
FIG. 28 shows the conversion of anhydride-modified hemoglobin under different conditions.

The condition for modification of hemoglobin by anhydride is also optimized for different parameters including pH and mole ratio. FIG. 28 shows the conversion of anhydride-modified hemoglobin under different conditions. The preferred condition is at pH 9 and 30 equivalents.

The structure of the modified hemoglobin linked with 5FU conjugate containing disulfide as cleavable linker (Hb-5FU-disulfide (cleavable) conjugate) is shown in FIG. 29A. It has been demonstrated successfully that the modified hemoglobin is linked to 5FU via a cleavable disulfide linker as shown in a LC-MS experiment. FIG. 29B shows the LC-MS result.

For live-cell imaging or diagnostic imaging purpose, hemoglobin based 5FU conjugates are labeled with fluorescent dye e.g. fluorescein-6. FIG. 30 shows the (A) schematic scheme and (B) characterization of fluorescent-labeled 5FU modified hemoglobin conjugate with alkyl non-cleavable linker (Hb-5FU-alkyl(non-cleavable) FL conjugate) by ESI-MS method. FIG. 31 shows the (A) schematic scheme and (B) characterization of fluorescent-labeled 5FU modified hemoglobin conjugate with carbinolamine cleavable linker (Hb-5FU-carbinolamine (cleavable) FL conjugate) by ESI-MS method.

Figure 23C:
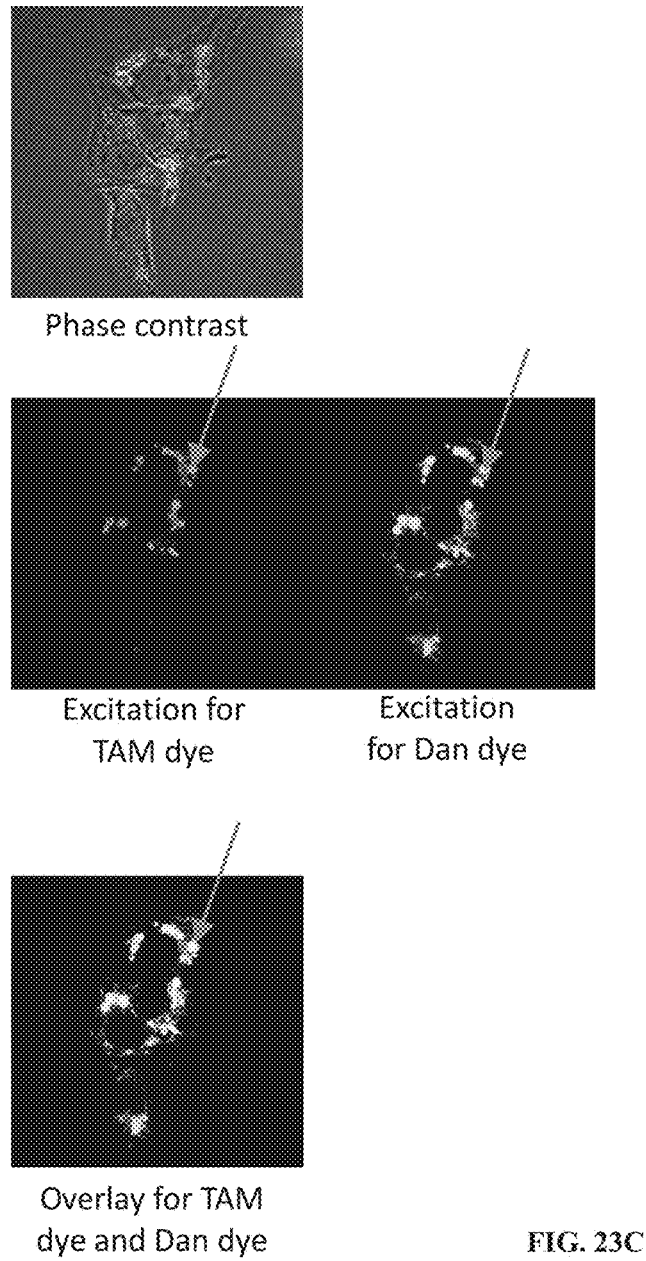
FIG. 23C illustrates that the Hb-5Fu-Dan-TAM conjugate labeled with two fluorescent dyes can enter into liver cancer cells successfully. Arrow indicates where the fluorescent signal (single or double fluorescent labeled) is detected from the cells under the microscope using different filter(s) of the microscope.

For imaging purpose, hemoglobin based-5FU conjugates are also labeled with two fluorescent dyes (shown in FIG. 32A). About 2 molecules of 5FU-dansyl and 2 molecules of TAMRA are conjugated onto one molecule of modified hemoglobin. A solution of modified hemoglobin solution (1 mL, 10 g/dL, 1.56 mM, DB buffer, pH 8.5) is added with 55 µL of TAMRA NHS (100 mM, 3.5 equiv.) in DMSO and 55 µL of 5FU-Dansyl NHS (100 mM, 3.5 equiv.) in DMSO. The reaction solution is stirred at room temperature for 4 hours, followed by purification usingbio-gel P-30 gel and characterization by ESI-MS (shown in FIG. 32B). The two-dye labeled 5FU modified hemoglobin conjugate (Hb-5FU-Dan-TAM) can also be uptaken in a similar manner as hemoglobin based 5FU, where both Dansyl-5FU (excitation at 488 nm) and TAM-Hemoglobin-based agent (excitation at 555 nm) are detected in the cytoplasm of the cancer cells (FIG. 23C).

No hemoglobin-based therapeutic agent is available in the market. The modified hemoglobin-based therapeutic agent containing pharmaceutical composition prepared in this invention can target to the cancer cells with therapeutic effect. For uses in cancer treatment, the modified hemoglobin-based therapeutic agent containing pharmaceutical composition of the present invention serves as an anti-cancer agent to kill cancer cells. The modified hemoglobin-based therapeutic agent is a good candidate to be used in low dose and can be combined with other molecular targeting or cytotoxic agents.

EXAMPLES

The following examples are provided by way of describing specific embodiments of this invention without intending to limit the scope of this invention in any way.

Example 1a

Synthesis of Ketene

To a vigorously stirred solution of 5-hexyn-1-ol (4 mmol) and triethylamine (4.5 mmol) in dichloromethane (DCM) (100 mL), methylsulfonyl chloride (MsCl) (4.1 mmol in DCM) is added dropwise at 0° C. The mixture is then warmed to room temperature for stirring overnight. Sodium bicarbonate (aqueous) is poured into the reaction mixture and the organic phase is separated. The aqueous layer is extracted with DCM and the combined organic extracts are washed with water and brine, dried over magnesium sulfate ($MgSO_4$) and the solvent evaporated. The crude mesylate is purified by flash column chromatography (20% ethyl acetate in n-hexane) to yield colorless oil.

To a solution of mesylate (2 mmol) in acetone (60 mL), potassium iodide (2.5 mmol) is added in the reaction mixture and heated to reflux for 20 h. After cooling to room temperature, the precipitate is filtered off. The filter cake is washed with acetone (20 mL) and the solvent is evaporated. The residual oil is diluted with ether (100 mL) and washed with sodium thiosulfate solution (saturated, 10 mL). The aqueous solution is extracted with ether and the combined organic extracts are washed with brine, dried over anhydrous magnesium sulfate and the solvent is evaporated. The residue is fractionally distilled in vacuum to give the iodide compound 5-hexyn-1-iodide.

Lithium bis(trimethylsilyl)amide (1 M in hexane, 20 mL) is added dropwise to a solution of phenylacetic acid methyl ester (2.73 g, 18.2 mmol) in dried tetrahydrofuran (40 mL) at −78° C. After 1 h, the reaction mixture is warmed to 0° C., and 5-hexyn-1-iodide (4.16 g, 20 mmol) in dried tetrahydrofuran (5 mL) is added dropwise to the solution. After stirring at 0° C. for 1.5 h, the reaction mixture is quenched with water washed, with a saturated ammonium chloride solution, and extracted with diethyl ether. The organic layers are combined and dried over anhydrous magnesium sulfate to give 4.17 g of alkyne-functionalized ester.

A solution of alkyne-functionalized ester (4.17 g, 18.1 mmol) in methanol (100 mL) and water (2 mL) is treated with potassium hydroxide pellets (1.5 g, 27 mmol) and heated to reflux overnight. The reaction mixture was concentrated in vacuo. Water is added to the reaction mixture, which is subsequently washed with diethyl ether. The aqueous layer is collected and acidified with hydrochloric acid and then extracted with ether. The organic layers are combined, dried over anhydrous magnesium sulfate, and concentrated in vacuo to give alkyne-functionalized carboxylic acid as a colorless oil.

To a solution of alkyne-functionalized carboxylic acid (1.08 g, 5 mmol) in dried dichloromethane (5 mL) at room temperature was added oxalyl chloride (2 M in dichloromethane, 5 mL) and the reaction mixture is stirred for 2 h. The solvent is distilled under nitrogen atmosphere to give a light yellow oil. The light yellow oil is dissolved in dried tetrahydrofuran (10 mL), and dried triethylamine (6 mL, 20 mmol) is added dropwise to the solution at 0° C. The resulting mixture is stirred at 0° C. for 2 h. The salt formed is filtered under nitrogen atmosphere, and the filtrate is distilled at 110° C. (1 mmHg) to give ketene as bright yellow oil.

Example 1b

Modification of Peptide and Hemoglobin Using Ketene

In a 1.0 mL eppendorf tube, peptide YTSSSKNVVR solution in water (1 mM, 10 μL), ketene (10 equivalents, 1 μL of a 100 mM stock solution of ketene in dried tetrahydrofuran), and phosphate buffer (pH 6.3 and 7.4, 80 μL) are mixed. The reaction mixture is kept at room temperature for 2 h. The conversion of the peptide is determined from total ion count of LC-MS analysis of the reaction mixtures. Using MS/MS (tandem mass spectrometry) analysis, the N-terminal selectivity is determined.

In a 1.0 mL eppendorf tube, the stabilized hemoglobin solution in buffer (1.56 mM, 40 ketene (10, 20, 30, 40, and 50 equivalents, 100 mM stock solution of ketene in dried tetrahydrofuran), and phosphate buffer (pH 6.3, 7.4 and 9, 160 μL) are mixed. The reaction mixture is kept at room temperature overnight (one set at pH 9 at 37° C.). The conversions of the protein are determined from total ion count of LC-MS analysis of the reaction mixtures. FIG. 27 shows the conversion for ketene-modified hemoglobin under different conditions (pH, temperature, mole ratio). The preferred condition is at pH 9, 37° C. and 30 equivalents.

Example 2a

Synthesis of Anhydride

A solution of alkyne-functionalized carboxylic acid (100 mg, 0.46 mmol), (3-dimethyl aminopropyl)-3-ethylcarbodiimide hydrochloride (EDC) (180.5 mg, 0.94 mmol), and triethylamine (0.5 mmol) in dichloromethane (20 mL) is stirred at room temperature overnight. The reaction mixture is washed with water. The organic layer is dried over anhydrous magnesium sulfate and concentrated in vacuo, and the residue is purified by flash column chromatography (eluting with 4% ethyl acetate in n-hexane) to give anhydride.

Example 2b

Modification of Peptide and Hemoglobin Using Anhydride

In a 1.0 mL eppendorf tube, peptide YTSSSKNVVR solution in water (1 mM, 10 μL), anhydride (10 equivalents, 1 μL of a 100 mM stock solution of anhydride in dried tetrahydrofuran), and phosphate buffer (pH 6.3 and 7.4, 80 μL) are mixed. The reaction mixture is kept at room temperature for 2 h. The conversion of the peptide is determined from total ion count of LC-MS analysis of the reaction mixtures. Using MS/MS analysis, the N-terminal selectivity is determined.

In a 1.0 mL eppendorf tube, stabilized hemoglobin solution in buffer (1.56 mM, 40 μL), anhydride (10, 20, 30, 40, and 50 equivalents, 100 mM stock solution of anhydride in dried tetrahydrofuran), and phosphate buffer (pH 6.3, 7.4 and 9, 160 μL) are mixed. The reaction mixture is kept at room temperature overnight (one set at pH 9 at 37° C.). The conversions of the protein are determined from total ion count of LC-MS analysis of the reaction mixtures. FIG. 28 shows the conversion for anhydride-modified hemoglobin under different conditions (pH, temperature, mole ratio). The preferred condition is at pH 9 and 30 equivalents.

Example 3a

Synthesis of NHS Ester

A solution of alkyne-functionalized carboxylic acid (100 mg, 0.46 mmol), N-hydroxysuccinimide (NHS) (64.4 mg, 0.56 mmol), (3-dimethyl aminopropyl)-3-ethylcarbodiimide hydrochloride (EDC) (180.5 mg, 0.94 mmol), and 4-di(methylamino)pyridine (DMAP) (0.5 mg, catalytic amount) in dichloromethane (20 mL) is stirred at room temperature overnight. The reaction mixture is washed with water. The organic layer is dried over anhydrous magnesium sulfate and concentrated in vacuo, and the residue is purified by flash column chromatography (eluting with 50% ethyl acetate in n-hexane) to give NHS ester.

Example 3b

Modification of Peptide and Stabilized Hemoglobin Using NHS Ester

A 6.8 μl (10 nmol) of stabilized hemoglobin solution (100 mg/mL, 1.56 mM) or 10 μL of YTSSSKNVVR stock solution (1 mM) is added into a mixed solution of 180 μL PBS (pH 7.4, 10 mM) buffer with 5 μL dimethylsulfoxide (DMSO) in a 1.5 mL eppendorf tube (stabilized hemoglobin/ YTSSSKNVVR final concentration: 0.05 mM). Fresh NHS ester (0.8 mg) solution (2 mM) in dry tetrahydrofuran (1 mL) is added in portions of 0.5 μL (0.1 equivalents/portion, 10, 20 and 40 portions) or 1.0 μL (0.2 equivalents/portion, 5, 10 and 20 portions) per addition per 2 min and immediately followed by vortex. The addition is finished within 90 min and the reaction solution is allowed to keep at room temperature for another 2.5 h. Subsequently, 10 μL of ethanolamine solution (20 mM) in PBS (pH 7.4, 10 mM) buffer is added to the reaction solution to quench the remaining free NHS ester at room temperature for 3 h.

Example 4a

Modification of the Stabilized Hemoglobin with Fluorescein 6-NHS Ester

The stabilized hemoglobin solution (9.9 g/dL) is modified by fluorescein 6-carboxysuccinimidyl ester (F-6-NHS). The reaction conditions (pH, ratio, time, buffer) are optimized and the reaction mixture is characterized by LC-ESI MS. The stabilized hemoglobin solution is adjusted to different pH (pH 8.0, 8.3, 8.5, 8.8 and 9.0 respectively) by acetic acid (0.2 M) and sodium hydroxide (0.1 M) under nitrogen. Different equivalents (3, 5, 7, and 9 equiv. respectively) of F-6-NHS in DMSO is added dropwise to the stabilized hemoglobin solution and stirred for different reaction times (2, 3, 4, and 5 h respectively) under nitrogen in the dark. The excess F-6-NHS is removed by Bio Spin Tris 30 column (10 k) (or ultra amicon 4 mL: 3 k). The modified hemoglobin solution is stored in RA buffer (pH 7.5) and characterized by LC-ESI MS.

Example 4b

Conversion for F-6-NHS-Modified Hemoglobin Under Different pH

The conversion of each unit of F-6-NHS-modified hemoglobin under different pH (pH 8.0, 8.3, 8.5, 8.8, and 9.0) is optimized. The conversion is determined from total ion count of LC-MS analysis of the reaction mixtures. The modification is performed in the ratio of 3:1 for F-6-NHS to stabilized hemoglobin in 1 mL RA buffer for 4 h in the dark. The result is shown in FIG. 24. The preferred pH condition is carried out at 8.5. In FIG. 24, a=α chain, a1=α chain modified with mono-fluorescein, a2=α chain modified with di-fluorescein, a3=α chain modified with tri-fluorescein, 2a=α-α chain, 2a1=α-α chain modified with mono-fluorescein, 2a2=α-α chain modified with di-fluorescein, 2a3=α-α chain modified with tri-fluorescein, 2β=β-β chain, 2β1=β-β chain modified with mono-fluorescein, 2β2=β-β chain modified with di-fluorescein, 2β3=β-β chain modified with tri-fluorescein, 2β4=β-β chain modified with tetra-fluorescein, 2β'=β'-β' chain, 2β'1=β'-β' chain modified with mono-fluorescein, 2β'2=β'-β' chain modified with di-fluorescein, 2β'3=β'-β' chain modified with tri-fluorescein, 2β'4=β'-β' chain modified with tetra-fluorescein.

Example 4c

Conversion for F-6-NHS-Modified Hemoglobin at Different Ratios of F-6-NHS to Stabilized Hemoglobin The conversion of each unit of F-6-NHS-modified hemoglobin with different ratios of F-6-NHS to stabilized hemoglobin (3, 5, 7, and 9 equivalents) in 1 mL RA buffer at pH 8.5 for 4 h in the dark. The stabilized hemoglobin concentration is 9.9 g/dL. The conversion is determined from total ion count of LC-MS analysis of the reaction mixtures. The result is shown in FIG. 25. The preferred ratio for F-6-NHS to stabilized hemoglobin is 7:1.

Example 4d

Conversion for F-6-NHS-Modified Hemoglobin at Different Reaction Times

The conversion of each unit of F-6-NHS-modified hemoglobin with 7 equivalents of F-6-NHS to stabilized hemoglobin in 1 mL RA buffer of pH 8.5 for different reaction times (2, 3, 4, and 5 h) in the dark. The stabilized hemoglobin concentration is 9.9 g/dL. The conversion is determined from total ion count of LC-MS analysis of the reaction mixtures. The preferred reaction time is at 4 h.

Example 4e

Conversion for F-6-NHS-Modified Hemoglobin in Different Buffers

The conversion of each unit of F-6-NHS-modified hemoglobin with 7 equivalents of F-6-NHS to stabilized hemoglobin in different buffers (acetate, carbonate, and phosphate buffer) at pH 8.5 for 4 h in the dark. The stabilized hemoglobin concentration is 9.9 g/dL. The conversion is obtained from the ratio of the mass intensity of modified-unit with the sum of the mass intensity of the corresponding unit. The result is shown in FIG. 26. There is no significant difference on the conversion for using different types of buffers.

Example 5a

Synthesis of 5FU-Carbinolamine (Cleavable) NHS Ester

A solution of 5FU carbinolamine succinic acid (375 mg, 1.86 mmol), N-hydroxysuccinimide (299 mg, 2.60 mmol), N-(3-dimethylaminopropyl)-N'-ethylcarbodiimide hydrochloride (EDC, 499 mg, 2.60 mmol) and 4-dimethylaminopyridine (DMAP, 30 mg, catalyst.) in dichloromethane (20 mL) and dimethylformamide (DMF) (1 mL) is stirred at room temperature under $N_2$ atmosphere for 18 h. The precipitate is filtered to give the 5FU-carbinolamine (cleavable) NHS ester.

Example 5b

Modification of Hemoglobin with 5FU-Carbinolamine (Cleavable) NHS Ester

A 1 mL of modified hemoglobin solution (10 g/dL, 1.56 mM, DB buffer, pH 8.5) is added with 110 μL of 5FU-carbinolamine (cleavable) NHS ester (100 mM, 7 equivalents) in DMSO. The reaction solution is stirred at room temperature for 4 h, followed by purification using bio-gel P-30 gel and characterization by ESI-MS. The estimated conversion yield is 95%. About 6 molecules of 5-FU cleavable are conjugated onto one molecule of modified hemoglobin.

Example 6a

Synthesis of 5FU Non-Cleavable NHS Ester

To a solution of 5FU (1.00 g, 7.69 mmol) in DMF (6 mL), is added triethylamine (1.08 mL, 7.69 mmol) dropwise. After stirring for 10 minutes, methyl acrylate (1.38 mL, 15.4 mmol) is added dropwise. The reaction mixture is kept stirring at room temperature for 20 h. The crude mixture is concentrated in vacuo and purified by flash chromatography with silica gel (eluting with 5% MeOH/DCM) to give methyl ester as product. To a solution of methyl ester (650 mg, 3.00 mmol) is dissolved in 5% HCl (35 mL). The reaction mixture is heated under reflux for 3 h. When the reaction mixture is cooled, $H_2O$ (20 mL) is added and the organic layers are extracted with ethyl acetate (6×20 mL). The combined organic layers are then dried ($MgSO_4$), filtered and concentrated in vacuo. The residue is purified by flash chromatography (eluting with 10% MeOH/DCM).

A solution of the obtained product (375 mg, 1.86 mmol), N-hydroxysuccinimide (299 mg, 2.60 mmol), N-(3-Dimethylaminopropyl)-N'-ethylcarbodiimide hydrochloride (EDC, 499 mg, 2.60 mmol) and 4-dimethyl aminopyridine (DMAP, 30 mg, catalyst) in DCM (20 mL) and DMF (1 mL) is stirred at room temperature under $N_2$ atmosphere for 18 h. The precipitate is filtered to give 5FU-alkyl (non-cleavable) NHS ester.

Example 6b

Modification of Hemoglobin with 5FU Non-Cleavable NHS Ester

A 1 mL of modified hemoglobin solution (10 g/dL, 1.56 mM, DB buffer, pH 8.5) is added with 110 μL of 5FU non-cleavable NHS (100 mM, 7 equivalents) in DMSO (dimethyl sulfoxide). The reaction solution is stirred at room temperature for 4 h, followed by purification using bio-gel P-30 gel and characterization by ESI-MS. The estimated conversion yield is 95%. About 6 molecules of 5FU non-cleavable are conjugated onto one molecule of modified hemoglobin.

Example 7a

Synthesis of Cleavable 5FU Disulfide N-Hydroxysuccinimide Ester

To a solution of 5FU-1-propionic acid N-hydroxysuccinimide ester (179 mg, 0.6 mmol), 4-[[2-[(2-aminoethyl)dithio]ethyl]amino]-4-oxo-butanoic acid (126 mg, 0.5 mmol) in DMF (5 mL), is added triethylamine (0.25 mL, 0.75 mmol) dropwise. The reaction mixture is kept stirring at room temperature (25° C.) for 4 h. The crude mixture is concentrated in vacuo and purified by flash chromatography (eluting with 5% $CH_3OH/CH_2Cl_2$) to give product 5FU-disulfide (cleavable) succinic acid.

A solution of 5FU disulfide succinic acid (109 mg, 0.25 mmol), N-hydroxysuccinimide (58 mg, 0.5 mmol), N-(3-Dimethylaminopropyl)-N'-ethylcarbodiimide hydrochloride (EDC, 96 mg, 0.5 mmol) and 4-dimethylaminopyridine (DMAP, 1 mg, cat.) in DMF (5 mL) is stirred at room temperature (25° C.) under $N_2$ atmosphere for 12 h. The crude reaction mixture is concentrated in vacuo. The residue is purified by flash chromatography (eluting with 5% $CH_3OH/CH_2Cl_2$) to give product 5FU-disulfide (cleavable) NHS ester as a white solid.

Example 7b

Modification of Hemoglobin with 5FU-Disulfide (Cleavable)-NHS

A 1 mL of modified hemoglobin solution (10 g/dL, 1.56 mM, DB buffer, pH 8.5) is added with 110 μL of 5FU-disulfide (cleavable) NHS ester (100 mM, 7 equivalents) in DMSO. The reaction solution is stirred at room temperature for 4 h, followed by purification using bio-gel P-30 gel and characterization by ESI-MS. About 4 molecules of 5FU disulfide are conjugated onto one molecule of modified hemoglobin.

Example 8

Synthesis of Temozolomide Disulfide N-Hydroxysuccinimide Ester

To a stirred solution of temozolomide acid N-hydroxysuccinimide ester (146 mg, 0.5 mmol) and 4-[[2-[(2-aminoethyl)dithio]ethyl]amino]-4-oxo-butanoic acid (126 mg, 0.5 mmol) in dry DMF (5 mL) in an ice water bath is added dropwise triethylamine (0.3 mL, 0.55 mmol). The mixture is warmed up to room temperature (25° C.) and then stirred for 4 h. The crude reaction mixture is concentrated in vacuo. The residue is purified by flash chromatography (eluting with 40% $CH_3OH/CH_2Cl_2$) to give product temozolomide disulfide succinic acid as white solid.

A solution of temozolomide disulfide succinic acid (78.5 mg, 0.18 mmol), N-hydroxysuccinimide (31 mg, 0.27 mmol) and N-(3-Dimethylaminopropyl)-N'-ethylcarbodiimide hydrochloride (EDC, 52 mg, 0.27 mmol) in DMF (1 mL) is stirred at room temperature (25° C.) under $N_2$ atmosphere for 12 h. The crude reaction mixture is concentrated in vacuo. The residue is purified by flash chromatography (eluting with 5% $CH_3OH/CH_2Cl_2$) to give product temozolomide disulfide N-hydroxysuccinimide ester as white solid.

Example 9

Modification of Hemoglobin with Fluorescein 6-NHS and 5FU Cleavable NHS Ester

A 1 mL of modified hemoglobin solution (10 g/dL, 1.56 mM, DB buffer, pH 8.5) is added with 55 μL of fluorescein 6-NHS (100 mM, 3.5 equivalents) in DMSO and 55 μL of 5FU cleavable NHS (100 mM, 3.5 equivalents) in DMSO. The reaction solution is stirred at room temperature for 4 h, followed by purification using bio-gel P-30 gel and characterization by ESI-MS. About 2.5 molecules of 5FU cleavable and 2.5 molecules of fluorescein are conjugated onto one molecule of modified hemoglobin.

Example 10

Modification of Hemoglobin with Fluorescein 6-NHS and 5FU Non-Cleavable NHS Ester (Labeled with One Fluorescent Dye)

A 1 mL of modified hemoglobin solution (10 g/dL, 1.56 mM, DB buffer, pH 8.5) is added with 55 μL of fluorescein 6-NHS (100 mM, 3.5 equivalents) in DMSO and 55 μL of 5FU non-cleavable NHS (100 mM, 3.5 equivalents) in DMSO. The reaction solution is stirred at room temperature for 4 h, followed by purification using bio-gel P-30 gel and characterization by ESI-MS. About 2.5 molecules of 5FU non-cleavable and 2.5 molecules of fluorescein are conjugated onto one molecule of modified hemoglobin.

Example 11

Synthesis of Different Compounds for Hemoglobin-5FU-Two-Dye Conjugate (Labeled with Two Fluorescent Dyes) for Live-Cell Imaging For synthesis of hemoglobin-5FU-Two-dye Conjugate for Live-Cell Imaging, precursors include copper lysine complex, 5FU lysine, 5FU dansyl lysine, 5FU dansyl lysine NHS ester, 5FU dansyl lysine ethanolamine, 5FU dansyl lysine succinic acid, 5FU dansyl lysine NHS ester.

Example 11a

Formation of Copper Lysine Complex

To a solution of L-lysine (3.14 g, 17.2 mmol) in sodium hydrogencarbonate solution (1 M, 40 mL), is added copper (II) sulphate (pentahydrate, 2.15 g, 8.60 mmol) in single portion. The dark blue suspension is stirred for 3 h prior to addition of methanol (15 mL). The reaction is left stirring for 24 h at room temperature. The resulting blue slurry is filtered and dried in vacuo to give copper-lysine complex (blue powder).

Example 11b

Formation of 5FU Lysine

Copper lysine complex (72.4 mg, 0.21 mmol) and sodium bicarbonate (34.4 mg, 0.41 mmol) are dissolved in $H_2O$ (5 mL). After 1 h of stirring at room temperature, 5FU-alkyl (non-cleavable) NHS ester (123 mg, 0.41 mmol) is added to the cloudy blue suspension. Stirring continued at room temperature for 16 h, during which time a colour change to a clear light blue (with no precipitation) is observed. Sodium sulfide (16.4 mg, 0.21 mmol) is then added and the reaction mixture turned greyish-brown. The crude mixture is neutralized to pH 4 using dilute hydrochloric acid. The precipitate is then filtered and the remaining filtrate is concentrated in vacuo and washed with cold methanol (20 mL) The crude clear residue is obtained and is used in the next step without purification.

Example 11c

Formation of 5FU Dansyl Lysine

To a solution of 5FU lysine (271 mg, 0.82 mmol) in dimethylformamide (6 mL) at 0° C. is added triethylamine (2 mL) dropwise. After stirring for 15 min, 5-(dimethylamino)naphthalene-1-sulfonyl chloride (270 mg, 1.00 mmol) is added and a colour change from clear to greenish-brown is observed upon the addition. After stirring in the dark at room temperature for 24 h, the reaction mixture is concentrated in vacuo prior to purification by flash chromatography (eluting with 20% methanol/dichloromethane) to yield 5FU dansyl lysine as yellow solid.

Example 11d

Formation of 5FU Dansyl Lysine NHS Ester

To a solution of 5FU dansyl lysine (98.0 mg, 0.17 mmol) in dimethylformamide (3 mL), is added N-hydroxysuccinimide (50.4 mg, 0.26 mmol), N-(3-dimethylaminopropyl)-N'-ethylcarbodiimide hydrochloride (30.0 mg, 0.26 mmol) and 4-(dimethylamino)pyridine (4 mg, catalyst). The reaction mixture is stirred in the dark at room temperature for 18 h. After that, the reaction mixture is concentrated in vacuo prior to purification by flash chromatography (eluting with 20% methanol/dichloromethane) to yield 5FU dansyl lysine NHS ester as a yellow solid.

Example 11e

Formation of 5FU Dansyl Lysine Ethanolamine

To a solution of 5FU dansyl lysine NHS ester (103 mg, 0.16 mmol) in dimethylformamide (1.5 mL) at room temperature, is added ethanolamine (500 μL) dropwise. The reaction mixture is stirred in the dark for 12 h. After that, the reaction mixture is concentrated in vacuo prior to purification by flash chromatography (eluting with 20% methanol/dichloromethane) to yield 5FU dansyl lysine ethanolamine as a yellow solid.

Example 11f

Formation of 5FU Dansyl Lysine Succinic Acid

To a solution of 5FU dansyl lysine ethanolamine (28.0 mg, 0.05 mmol) in tetrahydrofuran (2 mL), is added triethylamine (0.50 mL) and succinic anhydride (40.0 mg, 0.42 mmol). The reaction mixture is heated to reflux for 3 h. Once cooled, the reaction mixture is concentrated in vacuo and is purified by flash chromatography (eluting with 20% methanol/dichloromethane) to yield 5FU dansyl lysine succinic acid as a yellow solid.

Example 11g

Formation of 5FU Dansyl Lysine NHS Ester

To a solution of 5FU dansyl lysine succinic acid (26.0 mg, 0.04 mmol) in dimethylformamide (1 mL), is added N-hydroxysuccinimide (18.0 mg, 0.07 mmol), N-(3-dimethylaminopropyl)-Y-ethylcarbodiimide hydrochloride (22.0 mg, 0.07 mmol) and 4-(dimethylamino)pyridine (2 mg, catalyst). The reaction mixture is stirred in the dark at room temperature for 20 h. The solvent is removed in vacuo and the crude residue is purified by flash chromatography (eluting with 20% methanol/dichloromethane) to yield 5FU dansyl lysine NHS ester as a yellow film.

Example 12

Modification of Hemoglobin with TAMRA-NHS and 5FU-Dansyl NHS Ester for Live Cell Imaging A 1 mL of modified hemoglobin solution (10 g/dL, 1.56 mM, DB buffer, pH 8.5) is added with 55 μL of TAMRA NHS (100 mM, 3.5 equivalents) in DMSO and 55 μL of 5FU-Dansyl NHS (100 mM, 3.5 equivalents) in DMSO. The reaction solution is stirred at room temperature for 4 h, followed by purification using bio-gel P-30 gel and characterization by ESI-MS. About 2 molecules of 5FU-Dans and 2 molecules of TAMRA are conjugated onto one molecule of modified hemoglobin.

Example 13

Culture and Reagents for Different Cancer Cell Lines

Cancer cells are cultured in DMEM (Invitrogen) with 10% Fetal bovine serum (FBS), 100 U/mL penicillin and 100 μg/mL streptomycin at 37° C. For normoxic condition, cells are incubated with ambient $O_2$ concentration and 5% $CO_2$; for hypoxic condition, cells are incubated with 0.1-0.5% $O_2$ (Quorum FC-7 automatic $CO_2/O_2/N_2$ gas mixer) and 5% $CO_2$. Culture conditions for both adherent and non-adherent cancer cell lines used are comparable, including liver cancer cells HepG2, Huh7 and SMMC7221, breast cancer cells 4T1, MCF7 and MDA-MB231, Glioblastoma brain cancer cells A172 and U87MG, Colorectal carcinoma cells HCT116 and HT29, leukemic cells H60 and Jurkat, Non-Small cell Lung cancer cells A549 and H460, Pancreatic cancer cells JF305 and Capan-1.

Example 14

Isolation, Culture and Reagents for Cancer Stem-Like/Progenitor Cells

Putative liver and breast cancer stem-like cells/progenitor cells (CD133+ LCSCs and CD44+/CD24− BCSCs) are sorted or isolated from human liver cancer cells using Flow Cytometric Analysis. These sorted cells have the potential to self-renew and differentiate, to be able to form tumours in NOD/SCID mice when injected with only a small numbers, to be able to form spheroids in vitro, and are highly chemoresistant in nature. Fluorescence Activated Cell Sorting (FACS) is performed on HepG2 liver cancer cells using PE-conjugated monoclonal mouse anti-human CD133 (BD Biosciences); and on MCF7 breast cancer cells using PE-conjugated monoclonal mouse anti-human CD24 and APC-conjugated monoclonal mouse anti-human CD44 (BD Biosciences). Isotypes IgG1k-PE, IgG2B-PE and IgG2Akappa-APC (Coulter Ltd.) serve as controls. Samples are analyzed and sorted on a FACS Aria II (BD Biosciences). The 25% most brightly stained or the bottom 25% most dimly stained cells are selected as positive and negative populations. Stemness of the sorted cells is verified by subsequent Western Blotting and staining of CD133, Oct 4 and Sox2 pluripotency markers.

The sorted LCSCs are subsequently transferred to non-adherent culture condition in human Mammocult basal medium (Stem Cell Technology Ltd.) supplemented with human Mammocult proliferation supplement (Stem Cell Technology Ltd.), 0.48 μg/mL freshly dissolved Hydrocortisone, and 4 μg/mL Heparin fresh before use. No antibiotics are added to the medium. The freshly prepared medium is filtered using 0.2 μm low-protein binding filters (Millipore Ltd). The LCSC spheroids are allowed to grow in suspension until they reach the size of about 70 μm in diameter. LCSC spheroids exceed the sizes of 70 μm are sub-cultured by centrifugation at 1000 rpm for 3 min, followed by physical dissociation with trypsin-EDTA for 1 min and subsequent re-suspension in new medium.

Example 15

Live Cell Time-Lapse Microscopy in Cancer Cells

Cancer cells (e.g. HepG2 liver cancer cells) are seeded onto glass bottom microwell dishes (MatTek Corporation). Live cells at defined zooms (63×, 20×) are acquired using Zeiss Observer Z1 widefield microscope, equipped with atmospheric/temperature-controlled chamber and motorized stage for multi-positional acquisition. The incubation is performed in an enclosed live cell imaging system purged with 0.1% $O_2$ and 5% $CO_2$ (premixed). Cells are exposed to (1) Hb-5FU-alkyl(non-cleavable)-FL conjugate, labeled with one fluorescent dye and (2) Hb-5Fu-Dan-TAM conjugate, labeled with two fluorescent dyes; for 15 min prior to the acquisition of images every 3 min for a period of 2 h. Images are deconvolved and compacted into time-lapse movies using the MetaMorph software (Molecular Device). The images are shown in FIGS. 23A, 23B and 23C.

Example 16

Cytotoxicity Assay on Cancer Cell Lines

Cell viability is measured using a 3-(4,5-dimethylthiazol-2-yl)-2,5-diphenyltetrazolium bromide (MTT) proliferation assay. Briefly, cancer cell lines (e.g. HepG2 or Huh7 liver cancer cells) are seeded in a 96-well flat-bottomed microplate (6000 cells/well) and cultured in 100 μL growth medium at 37° C. and 5% $CO_2$ for 24 h. Cell culture medium in each well is then replaced by 100 μL cell growth medium, containing either no drug, 5FU alone or modified hemoglobin-based 5FU (Hb-FU) with another chemotherapeutics at their $IC_{50}$ concentrations. Incubation of 5FU or Hb-FU for 24 h, 20 μL MTT labeling reagent (5 mg/mL in PBS solution) is added to each well for further 4 h at 37° C. The growth medium is removed gently, and 200 μL DMSO is then added to each well as solubilizing agent to dissolve the formazan crystals completely. The absorbance at the wavelength of 570 nm is measured by Multiskan EX (Theinio Electron Corporation), and each data point represents the means± SD from triplicate wells.

Example 17

Establishment of Various Tumor Xenograft Models in Immunodeficient Nude & NOD/SCID Mice and Dosing Regimen Human cancer cells are inoculated into balb/c nude mice to establish two subcutaneous tumor models. Animals are randomized and assigned into 9 different groups (4-8 mice per group) prior to treatments. Animals received either: (1) RA-buffer, (2) stabilized hemoglobin alone (4 doses, 1 dose per week) at 0.4 g/kg (for human: 0.03 g/kg) (intravenous injection, i.v.), (3) 5FU (4 doses, 1 dose per week) at 80 mg/kg (i.v.), (4) co-administration of 5FU and stabilized hemoglobin (stabilized hemoglobin given 1 h prior to 5FU treatment), (5) multiple doses of stabilized hemoglobin (stabilized hemoglobin given on day 1 and on day 4, for 4 weeks), (6) Non-cleavable form of stabilized hemoglobin conjugated with 5FU (4 doses, 1 dose per week) at 0.4 g/kg (i.v.), and (7) Cleavable forth of stabilized hemoglobin conjugated with 5FU (4 doses, 1 dose per week) at 0.4 g/kg (i.v.).

Tumorigenicity of the cancer cells is determined by subcutaneous injection of 1-5×10$^6$ of cancer cells into the flank of 5-week old balb/c nude mice. For cancer progenitor cells, 1×10$^5$ of successfully isolated progenitor cells are subcutaneously injected into the NOD/SCID mice for xenograft establishment. Each group contains four to eight animals. After tumors are detected at around 0.3-0.5 cm3, tumor size is measured every 3 days by calipers, and tumor volumes are calculated as volume (cm3)=(L×W×W)/2. Mice are weight on the day of sacrifice and harvested tumors are weighted and imaged immediately after sacrifice.

What is claimed is:
1. A method for preparing a hemoglobin-based therapeutic agent comprising:
contacting a chemical modifying agent selected from the group consisting of:
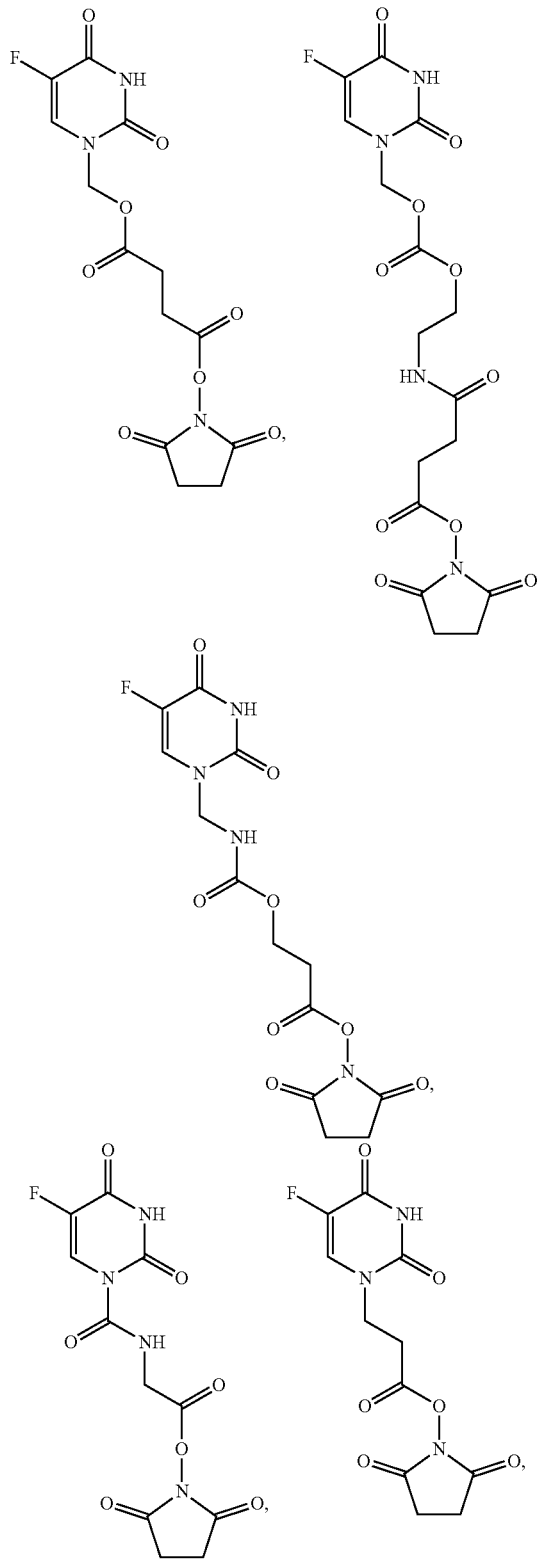
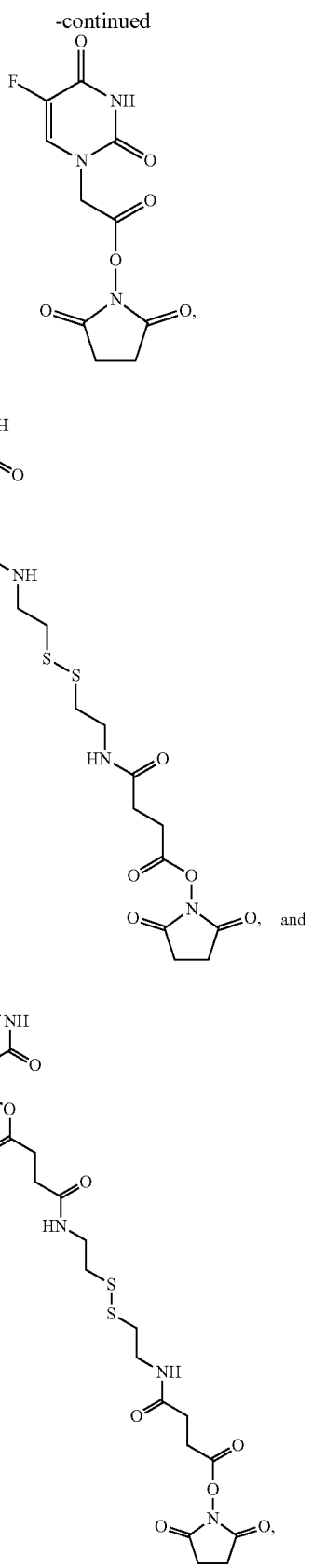
with a hemoglobin solution comprising a hemoglobin molecule thereby forming said hemoglobin-based therapeutic agent, wherein said hemoglobin-based therapeutic agent is selected from the group consisting of:

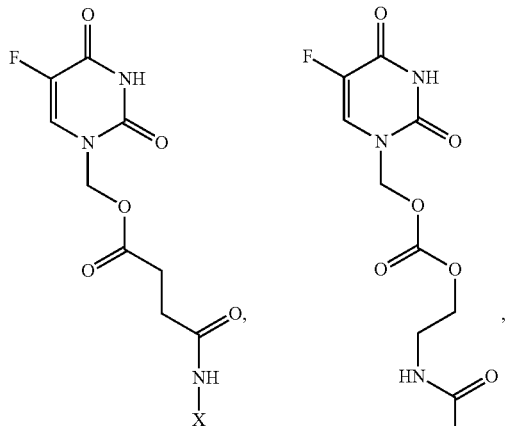

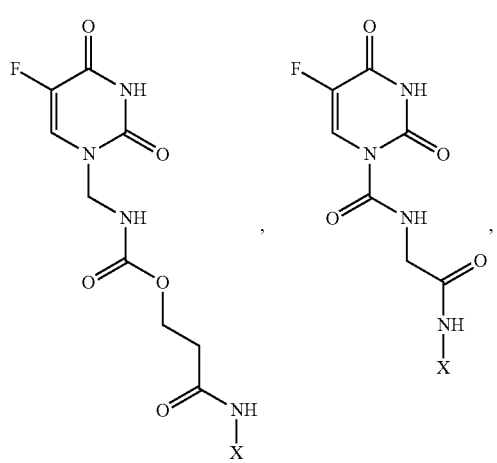

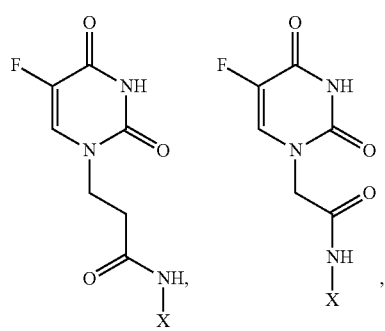

wherein X represents the hemoglobin molecule.

2. The method of claim 1, wherein said hemoglobin molecule is derived from bovine, human, canine, porcine, equine or recombinant hemoglobin molecule and/or the subunits thereof.

3. The method of claim 1, wherein said hemoglobin solution has a pH of 8.5.

4. The method of claim 1, wherein said chemical modifying agent has a mole ratio of 3-7:1 to said hemoglobin molecule.

* * * * *

SEQUENCE LISTING

<160> NUMBER OF SEQ ID NOS: 10

<210> SEQ ID NO 1
<211> LENGTH: 141
<212> TYPE: PRT
<213> ORGANISM: Bovine

<400> SEQUENCE: 1

Val Leu Ser Ala Ala Asp Lys Gly Asn Val Lys Ala Ala Trp Gly Lys
1               5                   10                  15

Val Gly Gly His Ala Ala Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Ala Lys Val Ala Ala
    50                  55                  60

Ala Leu Thr Lys Ala Val Glu His Leu Asp Asp Leu Pro Gly Ala Leu
65                  70                  75                  80

Ser Glu Leu Ser Asp Leu His Ala His Lys Leu Arg Val Asp Pro Val
                85                  90                  95

Asn Phe Lys Leu Leu Ser His Ser Leu Leu Val Thr Leu Ala Ser His
            100                 105                 110

Leu Pro Ser Asp Phe Thr Pro Ala Val His Ala Ser Leu Asp Lys Phe
        115                 120                 125

Leu Ala Asn Val Ser Thr Val Leu Thr Ser Lys Tyr Arg
    130                 135                 140

<210> SEQ ID NO 2
<211> LENGTH: 142
<212> TYPE: PRT
<213> ORGANISM: Homo sapiens

<400> SEQUENCE: 2

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Lys Lys Val Ala
    50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140

<210> SEQ ID NO 3
<211> LENGTH: 141
<212> TYPE: PRT
<213> ORGANISM: Canine

<400> SEQUENCE: 3

```
Val Leu Ser Pro Ala Asp Lys Thr Asn Ile Lys Ser Thr Trp Asp Lys
  1               5                  10                  15

Ile Gly Gly His Ala Gly Asp Tyr Gly Glu Ala Leu Asp Arg Thr
             20                  25                  30

Phe Gln Ser Phe Pro Thr Thr Lys Thr Tyr Phe Pro His Phe Asp Leu
         35                  40                  45

Ser Pro Gly Ser Ala Gln Val Lys Ala His Gly Lys Lys Val Ala Asp
     50                  55                  60

Ala Leu Thr Thr Ala Val Ala His Leu Asp Asp Leu Pro Gly Ala Leu
 65                  70                  75                  80

Ser Ala Leu Ser Asp Leu His Ala Tyr Lys Leu Arg Val Asp Pro Val
             85                  90                  95

Asn Phe Lys Leu Leu Ser His Cys Leu Leu Val Thr Leu Ala Cys His
            100                 105                 110

His Pro Thr Glu Phe Thr Pro Ala Val His Ala Ser Leu Asp Lys Phe
        115                 120                 125

Phe Ala Ala Val Ser Thr Val Leu Thr Ser Lys Tyr Arg
        130                 135                 140

<210> SEQ ID NO 4
<211> LENGTH: 141
<212> TYPE: PRT
<213> ORGANISM: Porcine

<400> SEQUENCE: 4

Val Leu Ser Ala Ala Asp Lys Ala Asp Val Lys Ala Ala Tyr Gly Lys
  1               5                  10                  15

Val Gly Ala His Ala Gly Glu Ala Gly Ala Glu Ala Leu Glu Arg Met
             20                  25                  30

Phe Leu Gly Phe Pro Thr Thr Lys Thr Tyr Phe Pro His Phe Asp Leu
         35                  40                  45

Ser His Gly Ser Asp Glu Val Lys Ala His Gly Glu Lys Val Ala Asp
     50                  55                  60

Ala Leu Thr Lys Ala Val Gly His Leu Asp Asp Met Pro Gly Ala Leu
 65                  70                  75                  80

Ser Ala Leu Ser Asp Leu His Ala His Lys Leu Arg Val Asp Pro Val
             85                  90                  95

Asp Phe Lys Leu Leu Ser His Cys Leu Leu Ser Thr Leu Ala Val His
            100                 105                 110

Leu Pro Asp Asp Phe Thr Pro Ala Val His Ala Asp Leu Asp Lys Phe
        115                 120                 125

Leu Ala Asp Val Ser Thr Val Leu Asp Ser Lys Tyr Arg
        130                 135                 140

<210> SEQ ID NO 5
<211> LENGTH: 142
<212> TYPE: PRT
<213> ORGANISM: Equine

<400> SEQUENCE: 5

Met Val Leu Ser Ala Ala Asp Lys Thr Asn Val Lys Ala Ala Trp Ser
  1               5                  10                  15

Lys Val Gly Gly His Ala Gly Glu Phe Gly Ala Glu Ala Leu Glu Arg
             20                  25                  30

Met Phe Leu Gly Phe Pro Thr Thr Lys Thr Tyr Phe Pro His Phe Asp
         35                  40                  45
```

Leu Ser His Gly Ser Ala Gln Val Lys Ala His Gly Lys Lys Val Gly
                50                  55                  60

Asp Ala Leu Thr Leu Ala Val Gly His Leu Asp Asp Leu Pro Gly Ala
 65                  70                  75                  80

Leu Ser Asn Leu Ser Asp Leu His Ala His Lys Leu Arg Val Asp Pro
                85                  90                  95

Val Asn Phe Lys Leu Leu Ser His Cys Leu Leu Ser Thr Leu Ala Val
                100                 105                 110

His Leu Pro Asn Asp Phe Thr Pro Ala Val His Ala Ser Leu Asp Lys
            115                 120                 125

Phe Leu Ser Ser Val Ser Thr Val Leu Thr Ser Lys Tyr Arg
        130                 135                 140

<210> SEQ ID NO 6
<211> LENGTH: 145
<212> TYPE: PRT
<213> ORGANISM: Bovine

<400> SEQUENCE: 6

Met Leu Thr Ala Glu Glu Lys Ala Ala Val Thr Ala Phe Trp Gly Lys
 1               5                  10                  15

Val Lys Val Asp Glu Val Gly Gly Glu Ala Leu Gly Arg Leu Leu Val
                20                  25                  30

Val Tyr Pro Trp Thr Gln Arg Phe Phe Glu Ser Phe Gly Asp Leu Ser
            35                  40                  45

Thr Ala Asp Ala Val Met Asn Asn Pro Lys Val Lys Ala His Gly Lys
 50                  55                  60

Lys Val Leu Asp Ser Phe Ser Asn Gly Met Lys His Leu Asp Asp Leu
 65                  70                  75                  80

Lys Gly Thr Phe Ala Ala Leu Ser Glu Leu His Cys Asp Lys Leu His
                85                  90                  95

Val Asp Pro Glu Asn Phe Lys Leu Leu Gly Asn Val Leu Val Val Val
                100                 105                 110

Leu Ala Arg Asn Phe Gly Lys Glu Phe Thr Pro Val Leu Gln Ala Asp
            115                 120                 125

Phe Gln Lys Val Val Ala Gly Val Ala Asn Ala Leu Ala His Arg Tyr
        130                 135                 140

His
145

<210> SEQ ID NO 7
<211> LENGTH: 147
<212> TYPE: PRT
<213> ORGANISM: Homo sapiens

<400> SEQUENCE: 7

Met Val His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Thr Pro Asp Ala Val Met Gly Asn Pro Lys Val Lys Ala His
 50                  55                  60

Gly Lys Lys Val Leu Gly Ala Phe Ser Asp Gly Leu Ala His Leu Asp
 65                  70                  75                  80

```
Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
            115                 120                 125

Ala Ala Tyr Gln Lys Val Val Ala Gly Val Ala Asn Ala Leu Ala His
        130                 135                 140

Lys Tyr His
145

<210> SEQ ID NO 8
<211> LENGTH: 141
<212> TYPE: PRT
<213> ORGANISM: Canine

<400> SEQUENCE: 8

Val Leu Ser Pro Ala Asp Lys Thr Asn Ile Lys Ser Thr Trp Asp Lys
1               5                   10                  15

Ile Gly Gly His Ala Gly Asp Tyr Gly Gly Glu Ala Leu Asp Arg Thr
            20                  25                  30

Phe Gln Ser Phe Pro Thr Thr Lys Thr Tyr Phe Pro His Phe Asp Leu
        35                  40                  45

Ser Pro Gly Ser Ala Gln Val Lys Ala His Gly Lys Lys Val Ala Asp
    50                  55                  60

Ala Leu Thr Thr Ala Val Ala His Leu Asp Asp Leu Pro Gly Ala Leu
65                  70                  75                  80

Ser Ala Leu Ser Asp Leu His Ala Tyr Lys Leu Arg Val Asp Pro Val
                85                  90                  95

Asn Phe Lys Leu Leu Ser His Cys Leu Leu Val Thr Leu Ala Cys His
            100                 105                 110

His Pro Thr Glu Phe Thr Pro Ala Val His Ala Ser Leu Asp Lys Phe
            115                 120                 125

Phe Ala Ala Val Ser Thr Val Leu Thr Ser Lys Tyr Arg
        130                 135                 140

<210> SEQ ID NO 9
<211> LENGTH: 147
<212> TYPE: PRT
<213> ORGANISM: Porcine

<400> SEQUENCE: 9

Met Val His Leu Ser Ala Glu Glu Lys Glu Ala Val Leu Gly Leu Trp
1               5                   10                  15

Gly Lys Val Asn Val Asp Glu Val Gly Gly Glu Ala Leu Gly Arg Leu
            20                  25                  30
```

```
Leu Val Val Tyr Pro Trp Thr Gln Arg Phe Phe Glu Ser Phe Gly Asp
            35                  40                  45

Leu Ser Asn Ala Asp Ala Val Met Gly Asn Pro Lys Val Lys Ala His
        50                  55                  60

Gly Lys Lys Val Leu Gln Ser Phe Ser Asp Gly Leu Lys His Leu Asp
65                  70                  75                  80

Asn Leu Lys Gly Thr Phe Ala Lys Leu Ser Glu Leu His Cys Asp Gln
                85                  90                  95

Leu His Val Asp Pro Glu Asn Phe Arg Leu Leu Gly Asn Val Ile Val
                100                 105                 110

Val Val Leu Ala Arg Arg Leu Gly His Asp Phe Asn Pro Asn Val Gln
            115                 120                 125

Ala Ala Phe Gln Lys Val Val Ala Gly Val Ala Asn Ala Leu Ala His
        130                 135                 140

Lys Tyr His
145

<210> SEQ ID NO 10
<211> LENGTH: 147
<212> TYPE: PRT
<213> ORGANISM: Equine

<400> SEQUENCE: 10

Met Val Gln Leu Ser Gly Glu Glu Lys Ala Ala Val Leu Ala Leu Trp
1               5                   10                  15

Asp Lys Val Asn Glu Glu Glu Val Gly Gly Glu Ala Leu Gly Arg Leu
            20                  25                  30

Leu Val Val Tyr Pro Trp Thr Gln Arg Phe Phe Asp Ser Phe Gly Asp
            35                  40                  45

Leu Ser Asn Pro Gly Ala Val Met Gly Asn Pro Lys Val Lys Ala His
        50                  55                  60

Gly Lys Lys Val Leu His Ser Phe Gly Glu Gly Val His His Leu Asp
65                  70                  75                  80

Asn Leu Lys Gly Thr Phe Ala Ala Leu Ser Glu Leu His Cys Asp Lys
                85                  90                  95

Leu His Val Asp Pro Glu Asn Phe Arg Leu Leu Gly Asn Val Leu Val
                100                 105                 110

Val Val Leu Ala Arg His Phe Gly Lys Asp Phe Thr Pro Glu Leu Gln
            115                 120                 125

Ala Ser Tyr Gln Lys Val Val Ala Gly Val Ala Asn Ala Leu Ala His
        130                 135                 140

Lys Tyr His
145
```